United States Patent [19]
Shioiri et al.

[11] Patent Number: 6,128,945
[45] Date of Patent: Oct. 10, 2000

[54] GAS DETECTING METHOD AND ITS DETECTOR

[75] Inventors: Akira Shioiri, Hyogo; Toshihiro Udaka, Kobe; Kazuya Shinnishi, Hyogo; Kazuko Takamatsu, Osaka, all of Japan

[73] Assignee: Figaro Engineering Inc., Osaka, Japan

[21] Appl. No.: 09/145,130

[22] Filed: Sep. 1, 1998

[30] Foreign Application Priority Data

Sep. 3, 1997 [JP] Japan ................................. 9-256047

[51] Int. Cl.$^7$ ............................ G01N 9/00; G01N 27/00; G01N 19/00
[52] U.S. Cl. ............................... 73/31.06; 422/98; 702/22
[58] Field of Search ............................ 73/25.01, 31.06, 73/31.07, 23.2; 422/98, 99; 702/22, 24

[56] References Cited

U.S. PATENT DOCUMENTS

| | | | |
|---|---|---|---|
| 4,562,723 | 1/1986 | Hubner | 73/31.07 |
| 4,627,269 | 12/1986 | Forster et al. | 73/31.06 |
| 5,007,283 | 4/1991 | Ambos | 73/1.07 |
| 5,305,231 | 4/1994 | Coppler et al. | 364/497 |
| 5,841,021 | 11/1998 | DeCastro et al. | 73/23.2 |

FOREIGN PATENT DOCUMENTS

| | | |
|---|---|---|
| 1-150850 | 6/1989 | Japan . |
| 8-101151 | 4/1996 | Japan . |
| 8-101153 | 4/1996 | Japan . |

OTHER PUBLICATIONS

Analytical Chemistry, vol. 68, No. 13, Jul. 1, 1996, P.2067–2072, "Gas Sensing Based on a Nonlinear Response: Discrimination between Hydrocarbons and Quantifiation of Individual . . ".

*Primary Examiner*—Hezron Williams
*Assistant Examiner*—Jay L. Politzer
*Attorney, Agent, or Firm*—Arent Fox Kintner Plotkin & Kahn

[57] ABSTRACT

A metal oxide semiconductor is subjected to a temperature change, and signals measured at two timings in the course of the temperature change are used to define a two-dimensional topological space. In the topological space, two axis, an axis indicating the concentration of the gas to be detected and an axis corresponding to drift are defined, and the topological space is represented by an oblique coordinate system. The gas concentration is determined from projection of measured data onto the gas concentration axis.

10 Claims, 36 Drawing Sheets

CO 400ppm
CO 150ppm
CO 70ppm
CO 30ppm
LnRs0, LnRs6
20

| |
|---|
| (Measured) LnRs0, LnRs6, T |
| (STD.) LnRs0, LnRs6 (30ppm) |
| LnRs0, LnRs6 (70ppm) |
| (Calculated) [COA], F, J, K, L [COB], COHb M, N |

30

GAS DETECTING METHOD AND ITS DETECTOR

FIELD OF THE INVENTION

The present invention relates to detection of a gas with a metal oxide semiconductor gas sensor, and in particular, it relates to a technology of detecting a gas by subjecting a gas sensor to temperature change.

PRIOR ART

An $SnO_2$ type CO sensor TGS203 (TGS203 is a trade name of Figaro Engineering Inc.) is a metal oxide semiconductor gas sensor that uses temperature change. This gas sensor operates in cycles and every cycle has a period of 150 seconds. The first 60 seconds of the cycle are allotted to a higher temperature period, and the subsequent 90 seconds to a lower temperature period. The final temperature of the higher temperature period is 300° C., and the final temperature of the lower temperature period is 80° C. The concentration of CO is detected from the resistance of the metal oxide semiconductor at the end of the lower temperature period. The resistance of the sensor is substantially in inverse proportion to the CO concentration. The ratio of hydrogen sensitivity to CO sensitivity of the sensor is 1:10; for example, hydrogen concentration of 1000 ppm is equivalent to CO concentration of 100 ppm. The initial distribution of the resistance is from 1 to 10 k$\Omega$ in CO 100 ppm.

The present inventors have worked to improve the overall accuracy of a CO detector using TGS203 and to improve the detection accuracy twice or over with using the same sensor. A problem that the present inventors have worked on the drift of the sensor characteristics. The resistance of TGS203 doubles at the largest in about two months after the start of its service. After that, the resistance decreases to about one half of the initial value at the lowest in several years. As the resistance value of TGS203 is substantially in inverse proportion to the CO concentration, this drift means that the detected value of CO concentration fluctuates within a range of from twice to one half of the actual value.

Now, the relevant prior art will be described. It has been proposed by Yoshikawa, et al. to change the temperature of a gas sensor, treat the behavior of its resistance as a temperature waveform and translate the waveform into Fourier series to detect gases (Analytical Chemistry Vol 68, No. 13, 2067–2072, 1996). Many research works have been reported in relation to the combination of a signal of a higher temperature range of a gas sensor with that of a lower temperature range thereof (for example, U.S. Pat. No. 4,896,143 and U.S. Pat. No. 4,399,684).

SUMMARY OF THE INVENTION

One object of the present invention is to provide a fundamental technique for determining a gas concentration with combining gas sensor signals sampled in a course of a temperature change.

According to the present invention, a metal oxide semiconductor gas sensor, of which resistance changes with gas, is subjected to a temperature change, and signals of plural points in a temperature waveform according to the temperature change are used to detect a gas such as CO, ethanol, ammonia and steam. The kind of the gas sensor is not limited to the $SnO_2$ type. The $In_2O_3$ type, $WO_3$ type, etc. may be used. The target of detection is not limited to CO. Targets include various gases such as ammonia, ethanol, formaldehyde and steam. The temperature change is effected by changing the electric power applied to a heater of the gas sensor. The pattern of this electric power is called the heater waveform. Various heater waveforms such as square, sine, lamp waveforms can be used.

The present invention is characterized in that a topological space is defined by at least two gas sensor signals in the course of the temperature change, at the time of calibration, said at least two gas sensor signals are measured in plural concentrations of the gas to be detected, data showing locus in said topological space when the concentration of the gas to be detected is changed is stored, at the time of measurement, said at least two gas sensor signals are measured to determine a point in said topological space, and the gas concentration is determined from one of the projection from said point to said locus stored and the distance between said locus and said point.

Here the projection may be one parallel to an appropriate axis in the topological space, or one that is perpendicular to the locus. Use of the projection and the distance means that the gas concentration is determined by these two factors. For example, if the projection is in a certain direction, the data on the distance will be reflected in the projection, and there will be no need of using the distance. Hence in a broader concept, the gas concentration is determined from the positions of the point relative to the locus in the topological space.

The present invention is characterized in that in said topological space, an oblique coordinate system comprising a gas concentration axis along said locus and a noise axis corresponding to fluctuations in gas sensor characteristics is defined, and the gas concentration is determined from points projected, in parallel to said noise axis, onto said gas concentration axis from said topological point.

Preferably, the projection is limited according to the distance from the gas concentration axis. Projecting coordinates being extremely far away from the gas concentration axis will exceed the reliability of detection. Hence, for coordinates that are remote from the gas concentration axis, the projection is limited so as to keep noise compensation small. It is desirable to make the limitations of the projection asymmetrical between the area above and the area below the gas concentration axis. It is desirable that compensation towards a lower concentration is made more modestly relative to compensation towards a higher concentration.

When gas sensor signals at two points are combined, the sensitivity to a coexisting gas may be negative, and the calculated gas concentration may be reduced by the coexisting gas. To compensate for it, preferably, another topological space for compensating for effects of the coexisting gas is defined, and the coexisting gas is detected. Once the presence of the coexisting gas is detected, the effects of the coexisting gas can be easily compensated for by a look-up table or some other techniques.

One aspect of the present invention includes a detector for detecting a gas by subjecting a metal oxide semiconductor gas sensor, of which resistance changes with the gas, to the temperature change, said detector comprising a means for determining a topological space comprising at least two gas sensor signals in a course of the temperature change and storing, at the time of calibration, locus of topological points in said topological space in plural concentrations of the gas to be detected, a means for measuring, at the time of measurement, said at least two gas sensor signals and determining a point in said topological space, and a means for determining the gas concentration from said point determined relative to said locus stored.

Preferably, the means for storing said locus includes a means for defining, in said topological space, a gas concentration axis corresponding to the concentration of the gas to be detected and a noise axis corresponding to the fluctuation of the gas sensor characteristics, and said means for storing said loci stores these axes, and said means for determining the gas concentration determines the gas concentration by projecting said topological point measured along the noise axis onto said gas concentration axis.

Another aspect of the present invention is an apparatus for detecting CO from signals of a metal oxide semiconductor gas sensor in a lower temperature range by applying electric power with a rectangular waveform to a heater of the gas sensor, of which resistance changes with CO, and changing the temperature of the metal oxide semiconductor alternately between a higher temperature range and the lower temperature range, said apparatus comprising a means for sampling a gas sensor signal after the shift from the lower temperature range to the higher temperature range, in the early part of the higher temperature range, after an occurrence of a bottom of the resistance of the metal oxide semiconductor, and before the temperature of the metal oxide semiconductor reaching a constant temperature in the higher temperature range, and a CO detecting means for detecting CO by the gas sensor signal sampled in the early part of the higher temperature range and a gas sensor signal in the lower temperature range.

According to another aspect of the present invention, the metal oxide semiconductor gas sensor is subjected to, for example, a periodical temperature change, and at least two gas sensor signals in the course of the temperature change are used to define a topological space. At the time of calibration, the concentration of the gas to be detected is changed, and for example, the gas sensor is operated in a specified atmosphere of a constant temperature and a constant humidity to measure said two gas sensor signals. At least two gas sensor signals represent a point in this topological space, and as measurement is made in plural concentrations of the gas to be detected, the locus of topological points with the change in the concentrations of the gas to be detected at the time of calibration is obtained, and data corresponding to it are stored. At the time of measurement, a point is obtained in the topological space in a similar manner. If the gas sensor is not exposed to any disturbance, the topological point will be on said locus, and the gas concentration can be simply determined from its position on the locus. If the point is away from the locus, its distances indicates the strength of the disturbance. Hence a compensation may be given by using this distance. The compensation may take many forms. For example, of the axes comprising the topological space, except for the axis having a high correlation with the concentration of the gas to be detected, the topological point is projected, parallel to the remaining axis, onto the locus, and the gas concentration at the projected point is taken as a tentative gas concentration. Then a compensation corresponding to the distance between the projected point and the measured point is given to the tentative gas concentration to determine the gas concentration. Or, in said topological space, a gas concentration axis, i.e., said locus and a noise axis indicating effects of disturbance are determined, and the measured point is projected, in parallel with the noise axis, onto the locus to determined the gas concentration. As for the gas sensor signals, the resistance of a metal oxide semiconductor, its logarithm, or Fourier transformation, or Fourier series of the logarithm of the resistance may be used. For a gas sensor signal before Fourier transformation, its Fourier transformation is equivalent to the generating function of the gas sensor signal. Hence either the signal before Fourier transformation or the signal after Fourier transformation may be used freely. The topological space is a space of at least two dimensions, and the oblique coordinate system is a coordinate system of at least two dimensions. As for the noise axis, there are, for example, a drift axis that corresponds to long term changes of the sensor characteristics, and a humidity axis that corresponds to humidity changes.

The present inventors examined a method of detecting a gas with treating changes in gas sensor signals with a temperature change as a temperature waveform of the sensor signal. In particular, the present inventors examined a method of detecting a gas by a combination of signals at at least two points in the course of the temperature change. The present inventors found that when a topological space is determined by these two factors, and when variations in coordinates of sensor signals due to drift, etc. are examined, noises such as drift show a clear regularity; the coordinates shift along a specific axis. Here this axis is called a noise axis or drift axis.

When the concentration of a gas to be detected is changed, the coordinates in the topological space will change, and this axis is called a gas concentration axis. In general, the noise axis and the gas concentration axis do not orthogonally intersect with each other. Hence it is necessary to represent the topological space with an oblique coordinate system. When coordinates in the topological space are measured, the gas concentration may be calculated by projecting the measured coordinates onto the gas concentration axis.

In one aspect of the present invention, a metal oxide semiconductor gas sensor is subjected to the temperature change, comprising a higher temperature range and a lower temperature range, to detect CO. The temperature change is generated by, for example, giving electric power of a rectangular waveform to a heater of the gas sensor, but the waveform of the power may be sinusoidal or saw-tooth, or the like. The kind of the metal oxide semiconductor may be $SnO_2$, that is used in the embodiment, $In_2O_3$, ZnO, etc. The configuration of the sensor is arbitrary. As for the temperature change, one in which a higher temperature range and a lower temperature range are repeated alternately, in particular, one in which such an alteration is regularly repeated at a specified period are indicated in the embodiment. However, the temperature change is not limited to them. Heating to a higher temperature range is intended to get signals for compensation and to give heat cleaning to the metal oxide semiconductor. Hence it is possible to normally maintain the metal oxide semiconductor in the lower temperature range and heat it to the higher temperature range only when there is a possibility that CO is present. The possibility of presence of CO can be detected from a gas sensor signal generated at the lower temperature range. The lower temperature range may be the room temperature.

The present inventors found that a signal of an early part of a higher temperature range and a signal of a lower temperature range have high correlations with drift and humidity changes, and that effects of drift can be compensated by compensating the signal of the lower temperature range with the signal of the early part of the higher temperature range. The inventors also found that as for the signal of the early part of the higher temperature range, a signal is effective, that is generated after the occurrence of a bottom of resistance and before the metal oxide semiconductor temperature reaching a constant value, or when the metal oxide semiconductor temperature is still rising. When these signals are combined, the effects of drift of a gas sensor are compensated for. In the case of TGS203, for example, an overall accuracy of ±20%, in conversion to CO concentration, is attained. As the resistance of TGS203 increases twice at the largest due to drift, the above-mentioned accuracy means reduction of the error to about one fifth.

EMBODIMENT

The Gas Detector

Figure 1:
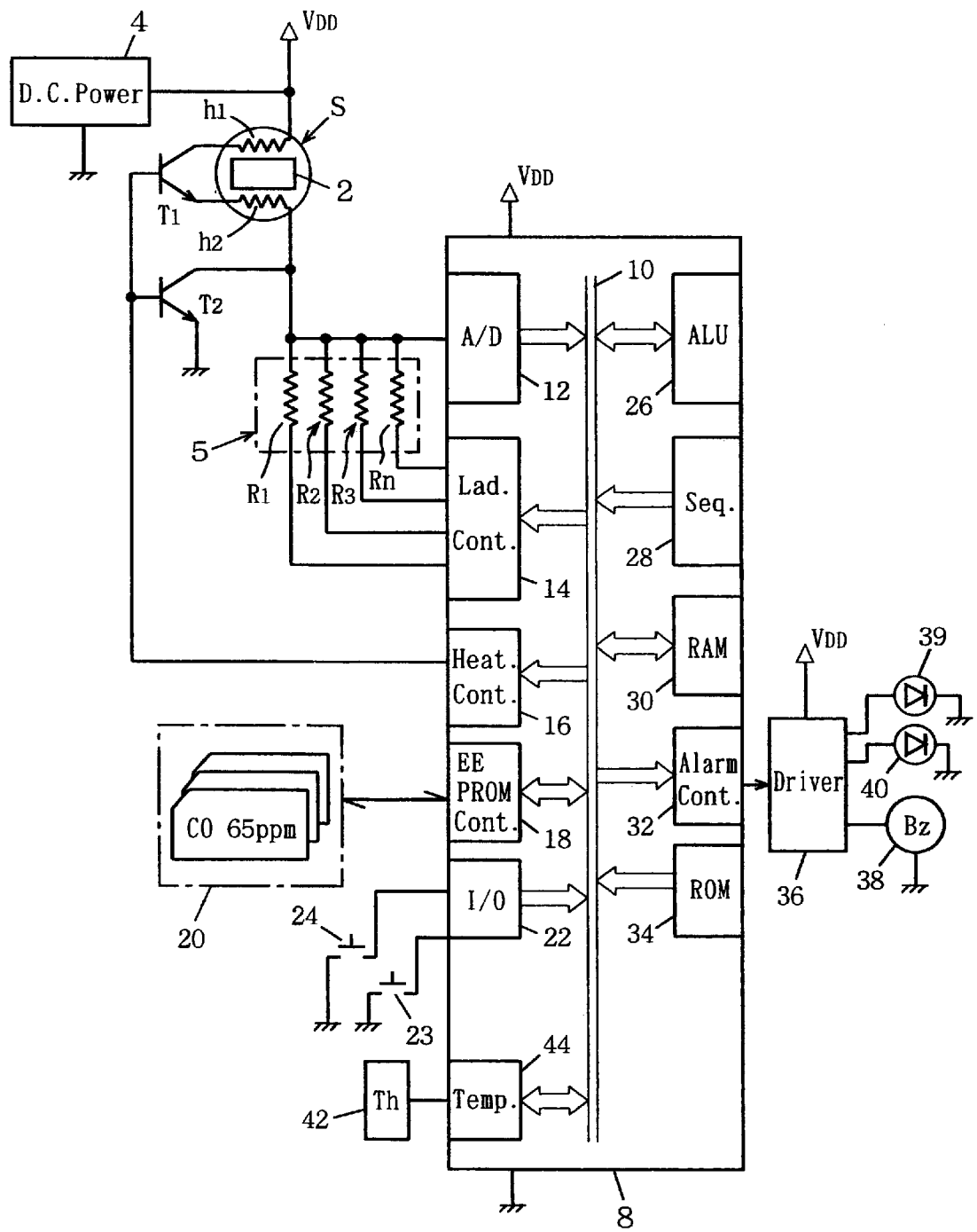
FIG. 1 is a lock diagram of a gas detector of an embodiment.

An embodiment and modifications thereof are shown in FIG. 1 through FIG. 24. The configuration of the embodiment is shown in FIG. 1. S denotes a metal oxide semiconductor gas sensor. Here TGS203 is used. It is an $SnO_2$ type metal oxide semiconductor 2 with a pair of heaters h1, h2 arranged at both ends thereof. The kind and configuration of the sensor S are arbitrary. 4 denotes a direct-current power source such as 5 V DC. Its output V DD is used to drive the gas detector. To drive the pair of heaters h1, h2 of the gas sensor S jointly, transistors T1, T2 are used; these transistors are turned on/off concurrently. When both the transistors T1, T2 are turned on, currents will flow through the heaters h1, h2. The temperature of the metal oxide semiconductor 2 is changed periodically by changing the duty ratio of on of the transistors T1, T2. Here, according to the operating conditions of TGS203, a higher temperature range is set for 60 seconds and a lower temperature range is set for 90 seconds. The waveform of the heater electric power is a rectangular waveform that changes between the higher temperature range and the lower temperature range. The final temperature of the higher temperature range is 300° C., and the final temperature of the lower temperature range is 80° C. In the embodiment, the time is expressed as follows: The 0th second is set at a point immediately before the completion of the lower temperature period. The period of from the 0th second to the 60th second is the higher temperature period, and the period of from the 60th second to the 150th second (the 150th second is also the 0th second) is the lower temperature period.

A ladder resistance 5 is connected to the metal oxide semiconductor 2, and R1 through Rn denote individual resistors thereof. Here, every resistor of R1 through Rn has a resistance that is four times as large as that of the immediately preceding resistor. For instance, are used six resistors; 0.5 kΩ, 2 kΩ, 8 kΩ, 32 kΩ, 128 kΩ and 512 kΩ. It is easy to obtain fixed resistors having an accuracy of about ±2%. Thus AD conversion error due to switchover of resistors is about ±2%. When the transistors T1, T2 are turned off, the power output V DD (hereinafter called the detecting voltage Vc) will flow, via the metal oxide semiconductor 2, to the ladder resistance 5. The output voltage to the ladder resistance 5 is AD-converted.

8 denotes a microcomputer. Here, a 4-bit one-chip microcomputer is assumed. 10 is the bus thereof. 12 is, for example, an 8-bit AD converter. 14 is a ladder resistance control. Only one resistor of the resistors R1 through Rn is earthed, and this earthed resistor is used as the load resistance. As described above, the output voltage to the ladder resistance is AD-converted by the AD converter 12. It is a matter of course that the output voltage to the ladder resistance 5 may be divided before AD conversion.

Moreover, the voltage on the sensor S side, rather than the voltage on the resistor ladder 5 side, may be AD-converted. 16 denotes a heater control that controls turning on/off of the transistors T1, T2 to generate the temperature cycle comprising the higher temperature range of 60 seconds and the lower temperature range of 90 seconds. 18 denotes an EEPROM control, and 20 denotes an EEPROM.

Figure 3:
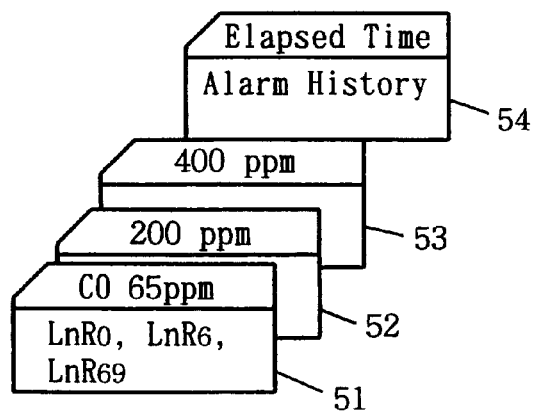
FIG. 3 a diagram showing the configuration of an EEPROM of the gas detector of the embodiment.

The configuration of the EEPROM 20 is shown in FIG. 3. Here it is assumed that, for example, the detection target is CO and the detection range is from CO 50 ppm through 600 ppm; the maximum is about ten times as large as the minimum. Standard signal sets are of three points; CO 65 ppm, 200 ppm and 400 ppm. Each set of standard signals comprises the logarithm of the sensor resistance at 0th second LnR0, the logarithm of the sensor resistance at the 6th second LnR6, and the logarithm of the sensor resistance at 69th second (the early part of the lower temperature period) LnR69. Ln denotes natural logarithm, and the subscript, such as 0 of R0, indicates the timing point measured from the 0 second. Similarly, three standard signals, logarithms of the sensor resistance values at the 0th second, the 6th second and the 69th second are stored for CO 200 ppm and CO 400 ppm, respectively. 51 through 53 denote cards. A set of standard signals for one concentration level are considered as a card. In addition to them, there is a card 54 on which are kept records of use of the CO detector. In other words, the total time of use and the past CO alarm records are stored on the card 54. The total time of use is the cumulative time when the power source of the CO detector was on. For example, the sample of time may be a day, and the cumulative time of use is stored in the card 54. As for records of alarm, whenever a buzzer, that will be described later, is made to buzz, the date will be recorded. As for this date, the same standard as the total time of use is used to record the date. With this arrangement, the date when the buzzer is activated can be identified.

22 denotes an input/output sample to which an adjusting switch 23 and a reset switch 24 are connected. When the adjusting switch 23 is turned on, the EEPROM control 18 will be able to write in EEPROM 20. This switch is used only when the CO detector is adjusted. The reset switch 24 is one for stopping the buzzer 38.

Figure 2:
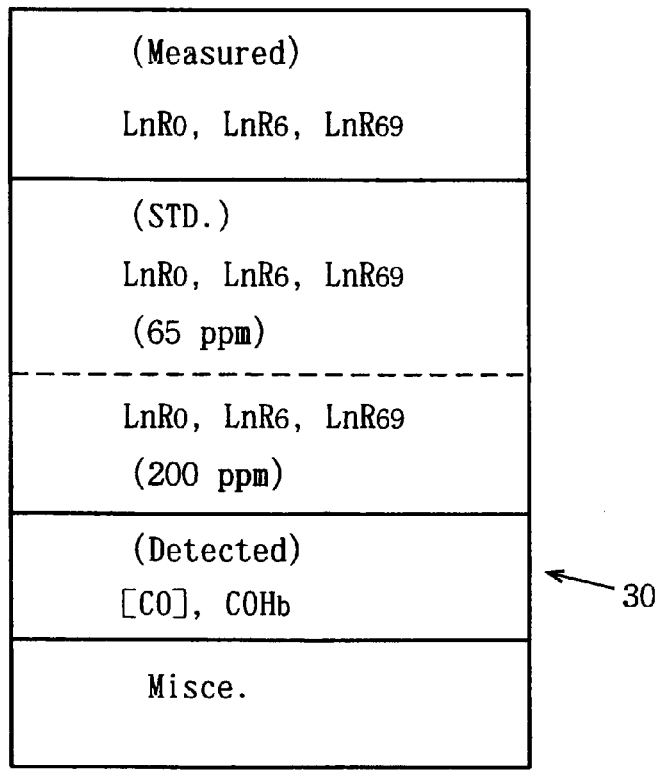
FIG. 2 diagram showing the configuration of a RAM of the gas detector of the embodiment.

The microcomputer 8 has a 4-bit arithmetic and logic sample 26. It also has a sequence control 28 for operating the CO detector at a cycle of 150 seconds. The sequence control 28 has a built-in timer. 30 denotes a RAM that is used as a volatile memory, and its configuration is shown in FIG. 2. In the RAM 30, are stored three pieces of measured data LnR0, LnR6 and LnR69 and corresponding standard signals for two concentrations. Normally are used standard signals for lower concentrations, 65 ppm and 200 ppm. When the gas concentration exceeds 200 ppm, the standard signals for 65 ppm will be replaced with those for 400 ppm. When the gas concentration drops to 200 ppm or under, the standard signals for 400 ppm will be replaced with those for 65 ppm. The gas detection range is from 50 to 600 ppm, and the range of from 50 to 65 ppm is close to the standard signal of 65 ppm. The range of from 400 to 600 ppm is 1.5 times as large as 400 ppm of the standard signals, and the gas concentration can be determined accurately by using the standard signals for 400 ppm. For the remaining range, when CO is generated, the gas concentration can be determined by using the standard signals for concentrations that are on both sides of the actual CO concentration to make interpolation between the two standard signals.

In the RAM 30, in addition to the above-mentioned data and signals, are stored a CO concentration determined, COHb (carbon monoxide hemoglobin concentration in blood) reduced from the CO concentration, and other auxiliary signals (for example, time data for constituting a timer of which sample is a day).

With reference to FIG. 1 again, 32 denotes an alarm control that actuates, via a drive circuit 36, LED 39 and LED 40. When the CO hemoglobin concentration in blood exceeds, for example, 5%, the alarm control 32 will actuate the buzzer 38. When the buzzer 38 is turned on, the EEPROM control 18 will write the date of the alarm in the card 54. 34 denotes a program memory in which data such as various constants for temperature compensation are stored. These data are fixed data common to the sensor S and other sensors. All the data for individual sensors are stored in the EEPROM 20. 42 denotes a thermistor that measures the ambient temperature. 44 denotes a temperature & humidity compensator.

Sampling and Logarithmic Transformation

Figure 4:
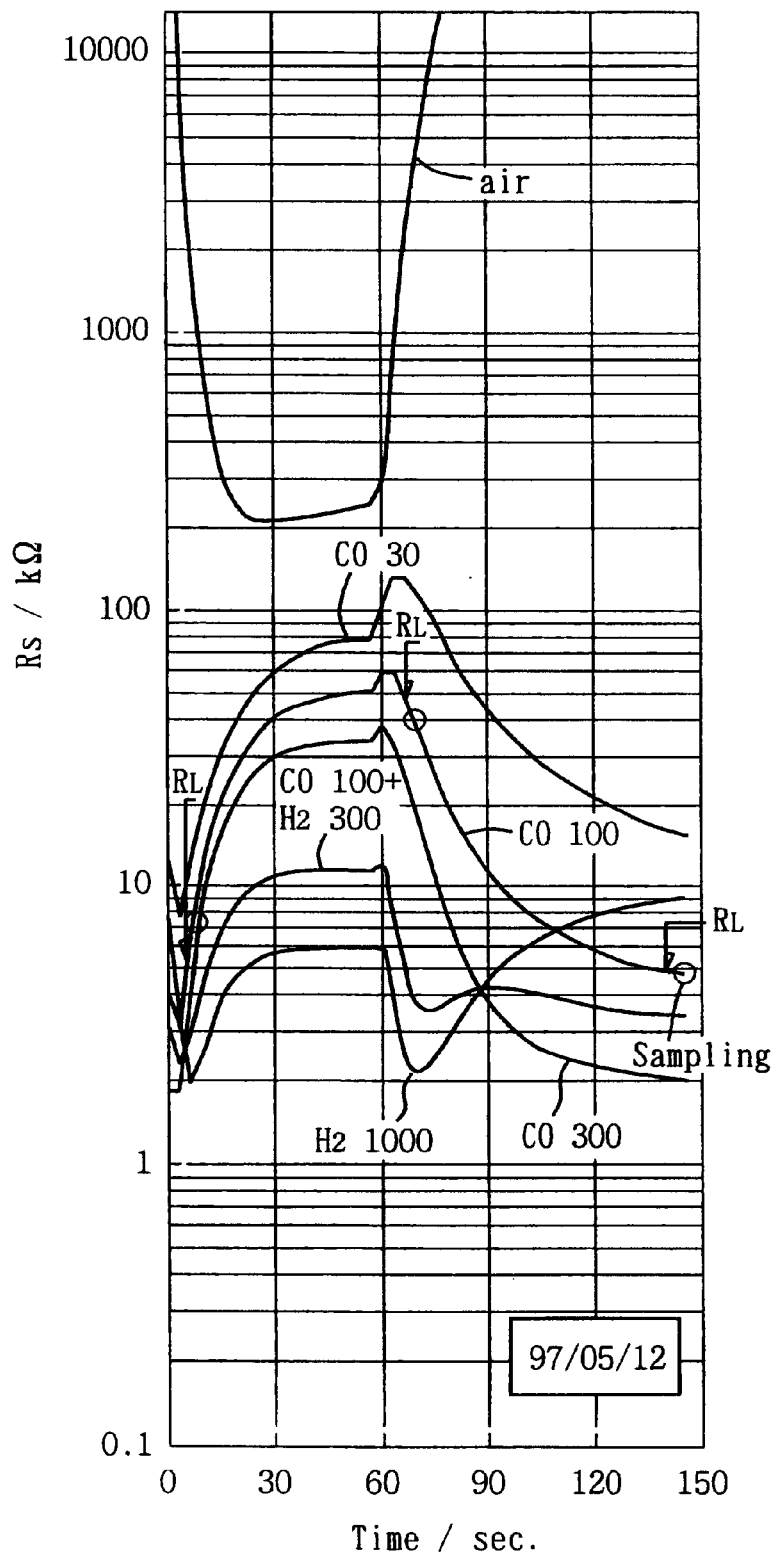
FIG. 4 is a characteristic diagram showing the waveform of the resistance of a gas sensor used in the embodiment.

Mean temperature waveforms of ten sensors are shown in FIG. 4. Sampling points, that are used in the embodiment, are marked by ○ on the waveform of CO 100 ppm; sampling is made at the 150th second, the 6th second and the 69th second. The sensor resistance changes by about ten times in the range of from CO 30 ppm to 300 ppm. The resistance at the 0th second and that at the 69th second differ from each other by a factor of about 10. When the dispersion in the sensor resistance, fluctuations in ambient temperature, humidity, etc. are added to them, the range of AD conversion is, in resistance, from about 0.5 to 500 k$\Omega$. To achieve AD conversion in this range, the resistances R1 through Rn are changed in six steps, ranging from 0.5 k$\Omega$ to 512 k$\Omega$, any resistance being four times greater than the immediately preceding one. Immediately before each sampling time, the output VR1 to the ladder resistance is monitored, and the load resistance is changed according to the output VR1. AD conversion of VR1 can be done within 1 second, and on the basis of the value at the time, use of which resistance at each sampling point can be determined.

Figure 5:
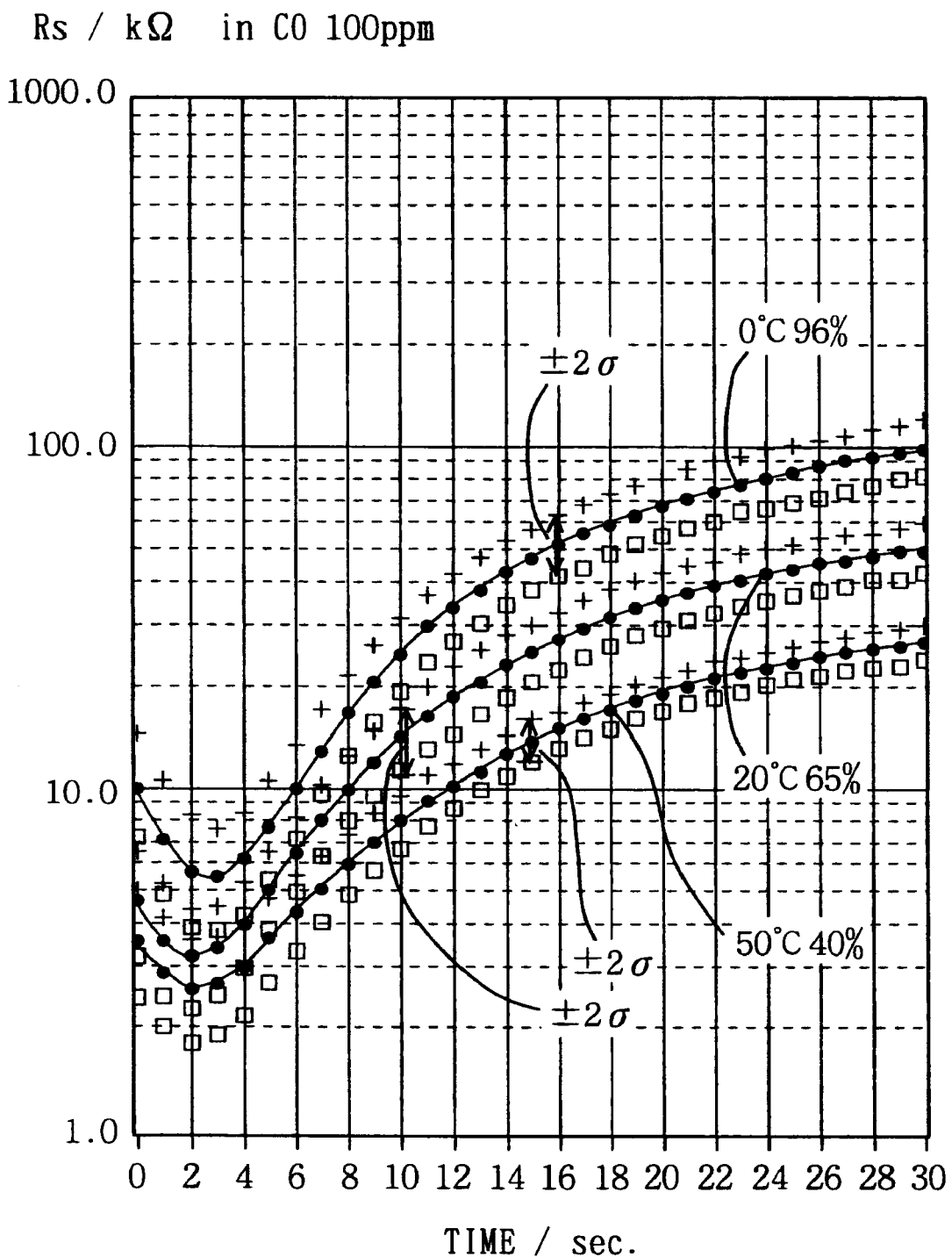
FIG. 5 is a characteristic diagram showing the resistance waveform in the early part of the higher temperature range of the gas sensor used in the embodiment.

FIG. 5 shows enlarged temperature waveforms of other ten sensors in the early part of the higher temperature range. The atmospheres are of three kinds; 0° C. and relative humidity of 96%, 20° C. and 65%, and 50° C. and 40%. The range of ±2$\delta$ ($\delta$ is the standard deviation) and the mean value are shown for each waveform. The gas concentration is CO 100 ppm. The resistance at each timing point varies by a factor of a little under 10 due to changes in ambient temperature and humidity. The resistance at the 0th second and the resistance at the 6th second are substantially identical to each other. Hence, for example, the same load resistance as that at the 0th second may be used for the 6th second. However, preferably, the resistance at the 0th second is determined from, for example, the signal at the 148th second (or at the 149th second to make more reliable sampling before the variation to the higher temperature range), and the load resistance at the 6th second is determined from the resistance at the 5th second. Similarly, the load resistance at the 69th second is determined from the resistance at the 68th second.

Figure 6:
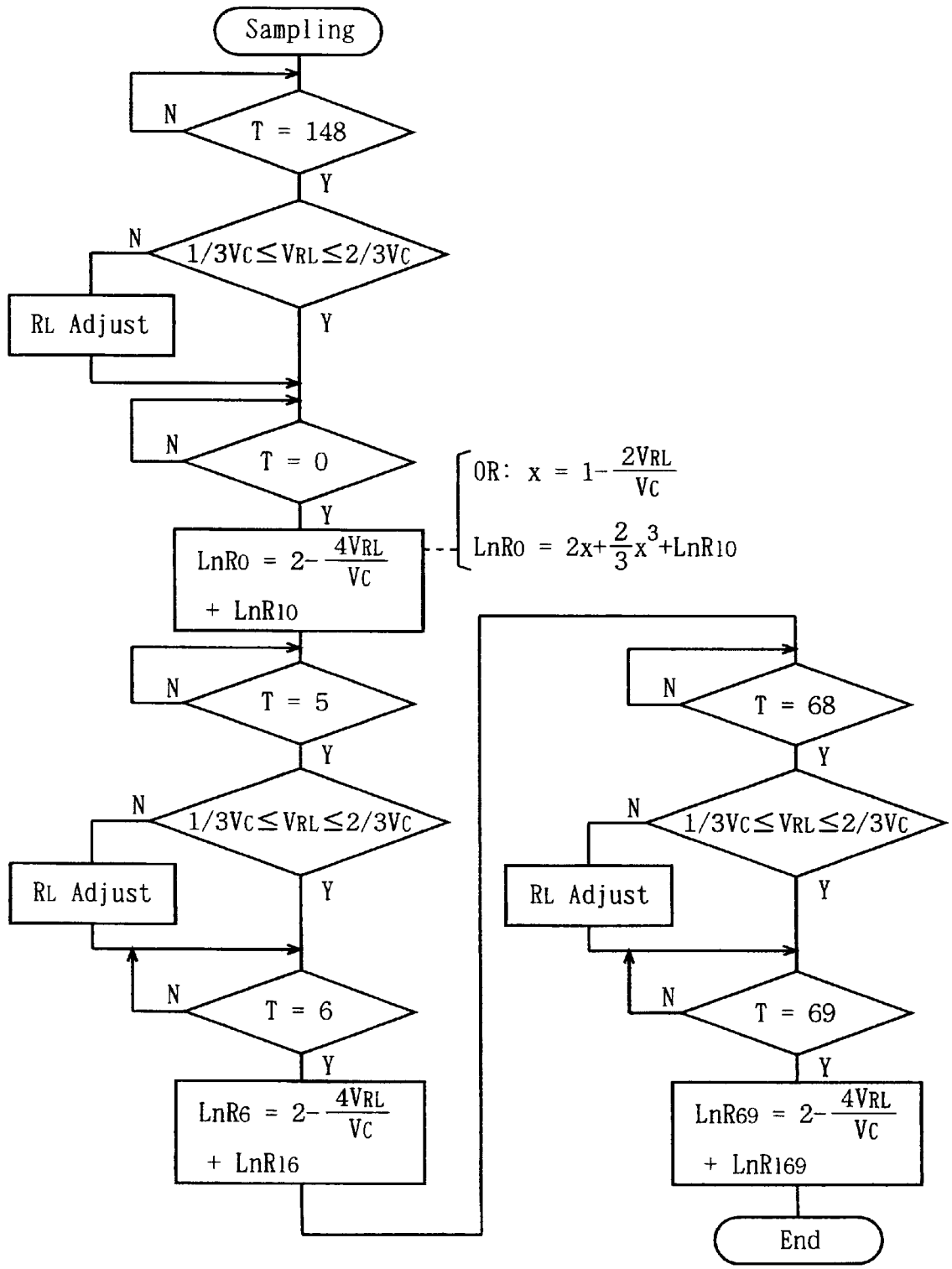
FIG. 6 is a flow chart showing the sampling algorithm of the gas detector of the embodiment.

FIG. 6 shows the algorithm of the sampling. When the time reaches the 148th second, the output voltage will be AD-converted, and this value will be checked whether it is within a range of from $\frac{1}{3}$ to $\frac{2}{3}$ of the detecting voltage Vc (identical to V DD). When the value is within this range, the ratio of the sensor resistance to the load resistance is within a range of from 2:1 to 1:2. If the output voltage is adequate, the same load resistance will be used. If the output voltage is not adequate, the load resistance will be changed to bring the output voltage within the above-mentioned range. Next, when the time reaches the 0th second, the output voltage will be AD-converted, and the AD-converted output voltage V R1 will be used to determine the logarithm of the sensor resistance at the 0th second by equation (1). Similarly, at the 5th second, the value of the load resistance is checked whether it is correct or not. Then the logarithm of the sensor resistance at the 6th second will be determined. Further, at the 68th second, the value of the load resistance is checked whether it is correct or not, and at the 69th second, the logarithm of the sensor resistance is determined.

$$LnR = 2 - 4V\,R1/Vc + LnR1 \quad (1)$$

If the logarithm of the sensor resistance is approximated up to the term of the first degree, as shown in equation (1), when R/R1 is 1, the error is 0, when R/R1 is $\frac{1}{2}$ or 2, the error is 2%, and when R/R1 is $\frac{1}{3}$ or 3, the error is 11%. In the embodiment, as it is aimed to detect the CO concentration with an error of ±20% or under, the error of ±10% is too large. Hence the ladder resistance 5 is controlled so that the ratio of the sensor resistance to the load resistance is within a range of from 2 to $\frac{1}{2}$ at three points of the 0th second, the 6th second and the 69th second.

The transformation of VR1 to the logarithm of the sensor resistance by equation (1) is a linear transformation and is a very simple transformation. However, this requires six load resistors. To reduce the number of load resistors required, for example, to four, it is necessary to keep R/R1 within a range of from 4 to $\frac{1}{4}$, or more preferably, within a range of from $\sqrt{8}$ to $1/\sqrt{8}$. For this, it is necessary to make transformation up to the term of third degree. When the logarithm of the sensor resistance is expanded into series with VR1, there will be no term of the second degree. We will have equations (2), (3) in which terms up to the third degree are considered. If equations (2), (3) are used, when R/R1 is 1, the transformation error is 0%, when R/R1 is $\frac{1}{4}$ or 4, the transformation error is 4%, and when R/R1 is $\frac{1}{3}$ or 3, the transformation error is 2%. Hence in resistors R1 through Rn, the resistance of the subsequent resistor is increased by 16 times, or preferably by 8 times or 9 times. For example, the resistance R1~Rn comprises 4 kinds, 1 k$\Omega$, 8 k$\Omega$, 64 k$\Omega$ and 512 k$\Omega$. With this arrangement, a range of from 0.5 to 1 M$\Omega$ can be transformed into logarithm with an error of 2% or under.

$$LnR = 2x + \frac{2}{3}xx^3 + LnR1 \quad (2)$$

$$x = 1 - 2VR1/Vc \quad (3)$$

Adjustment of the Gas Detector

Figure 7:
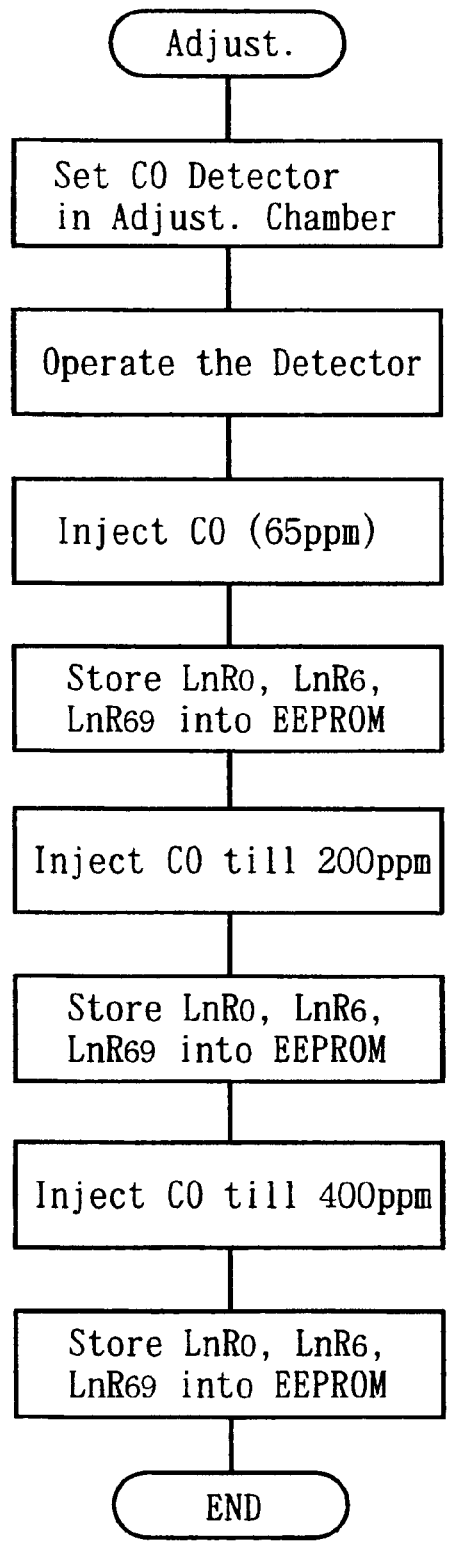
FIG. 7 is a flow chart showing the adjustment algorithm of the gas detector of the embodiment.

The procedure for adjusting the gas detector of FIG. 1 is shown in FIG. 7. At the time, the adjusting switch 23 is turned on so that standard signals can be written into the EEPROM 20. The procedure will be described by assuming that the CO detector is set in an adjusting chamber. After the CO detector is set, the power source is turned on to operate the detector. Next, CO is injected, for example, up to 65 ppm. Then the microcomputer 8 generates LnR0, LnR6 and LnR69 to write them into the RAM 30. They are written in the card 51 of the EEPROM 20. Next, the CO concentration is increased to 200 ppm, and similar steps are repeated. Then the CO concentration is increased to 400 ppm. In this way, by increasing the CO concentration with the specified steps, standard signals can be written into the EEPROM 20. Thus there is no need of adjusting a variable resistor to store a standard signal. The adjusting work can be done with ease.

It is assumed here that the CO detector is set in an adjusting chamber. However, only a sensor S may be set in an adjusting chamber. Then, the resistance of the sensor S is AD-converted by an AD converter of, for example, 12 bit, and it is stored in a personal computer or the like, and in turn, it is written into the EEPROM 20. In this case, the sensor S is not assembled into the CO detector, and the sensor S and the EEPROM are treated as a set. They are connected with a CO detector that is assembled separately. The portion of the CO detector other than the sensor S and the EEPROM 20 can be handled in the same manner as conventional electronic circuits, and even a manufacturer with no experience on gas sensors can assemble a CO detector.

Drift of Gas Sensor Signals

Drift characteristics of the sensor resistance are shown in FIG. 8 through FIG. 12. The data was taken from 45 samples of TGS203. These samples included defective samples (7 samples), non-defective samples (20 samples), samples that were left to stand for two or more years (8 samples), and samples that were set on CO detectors and recovered eventually (10 samples). The axis of abscissa of each diagram shows the sensor resistance at the 0th second on a logarithmic scale, and the axis of ordinate shows the sensor resistances at the 6th second (FIG. 8), 12th second (FIG. 9), 30th second (FIG. 10), 60th second (FIG. 11) and 120th second (FIG. 12) on a logarithmic scale. 1 on the axis of abscissa indicates the standard signal at the 0th second in CO 100 ppm (on the third day after the start of energization), and 1 on the axis of ordinate indicates the standard signal at the 6th second in CO 100 ppm (on the third day after the start of energization). FIG. 8 through FIG. 12 are normalized by standard signals that were generated in CO 100 ppm on the third day of energization.

Figure 8:
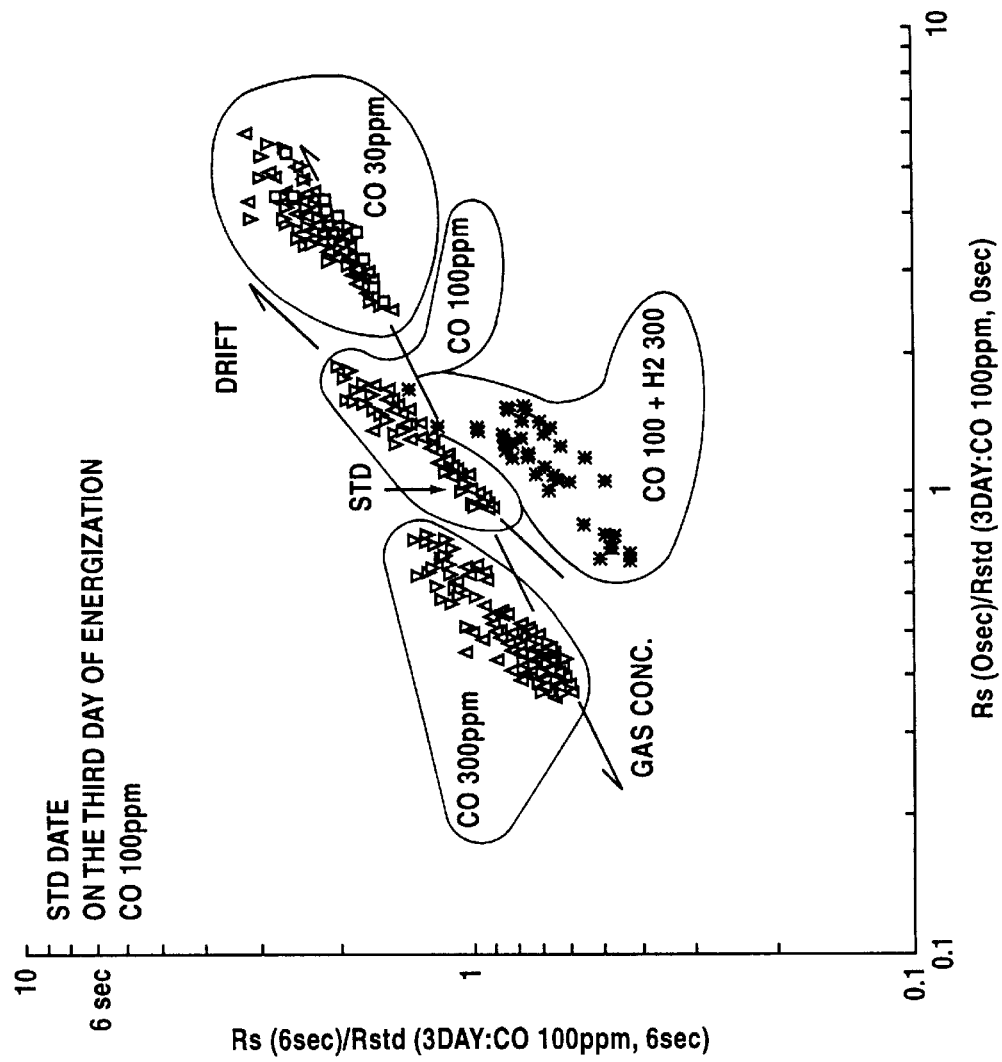
FIG. 8 is a characteristic diagram showing drift characteristics in a 0–6 sec plane in the embodiment.

The respective points on each diagram show the measuring points in the course of five weeks of energization. When 45 samples of TGS203 were used for five weeks, some samples increased in resistance and some others decreased in resistance by a factor of two. In FIG. 8, points of increased resistance concentrate on a narrow straight line having a gradient of 1 on a two-dimensional space of the 6th second resistance and the 0th second resistance. This axis is called a drift axis. Drift axes are not distinct for the data taken in CO 30 ppm and 300 ppm. This is due to variance of the concentration dependence of TGS203. As their concentration dependence is not homogeneous, the initial points in CO 30 ppm and 300 ppm do not coincide at one point. Because of variance of the initial points, their drift axes are indistinct. A straight line connecting three points of CO 30 ppm, 100 ppm and 300 ppm is called the concentration axis. The initial characteristics of TGS203 are on this concentration axis. With the use, the characteristics drift from the concentration axis parallel by to the drift axis.

Figure 9:
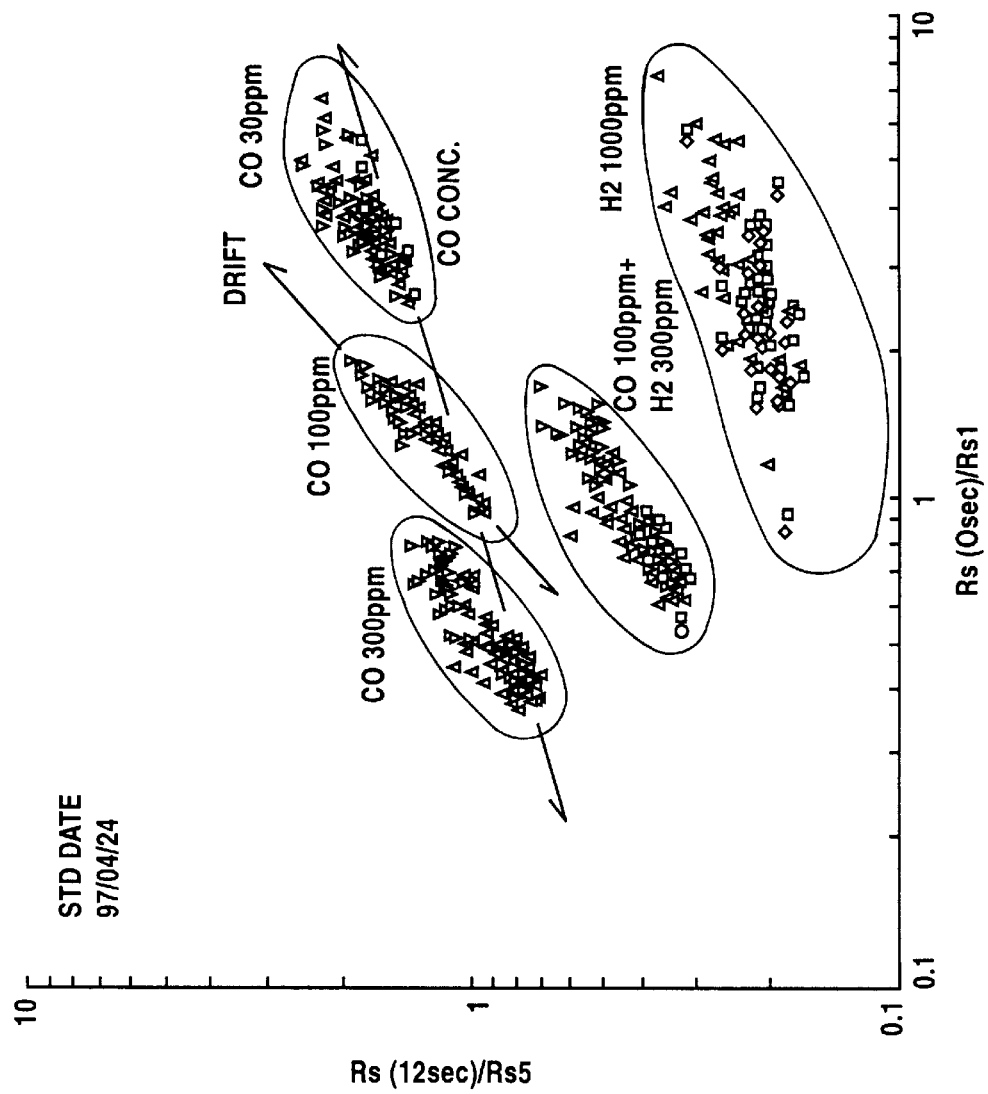
FIG. 9 is a characteristic diagram showing drift characteristics in a 0–12 sec plane in the embodiment.
Figure 10:
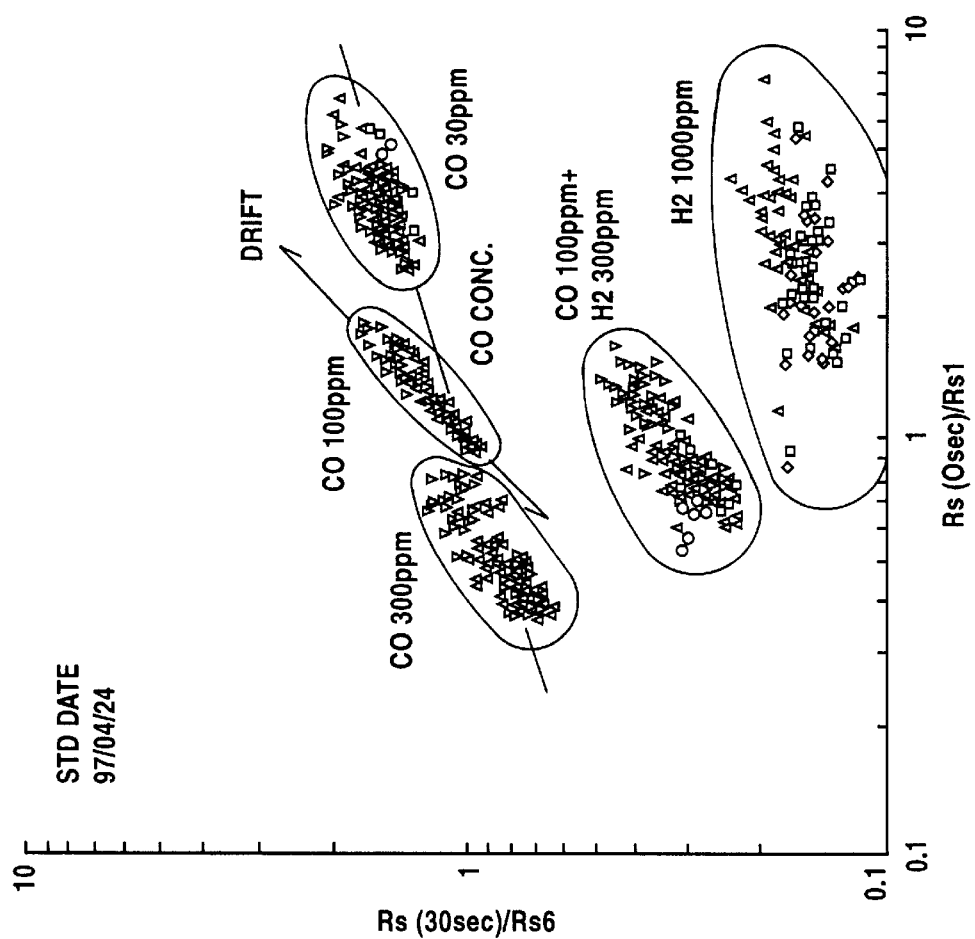
FIG. 10 is a characteristic diagram showing drift characteristics in a 0–30 sec plane in the embodiment.
Figure 11:
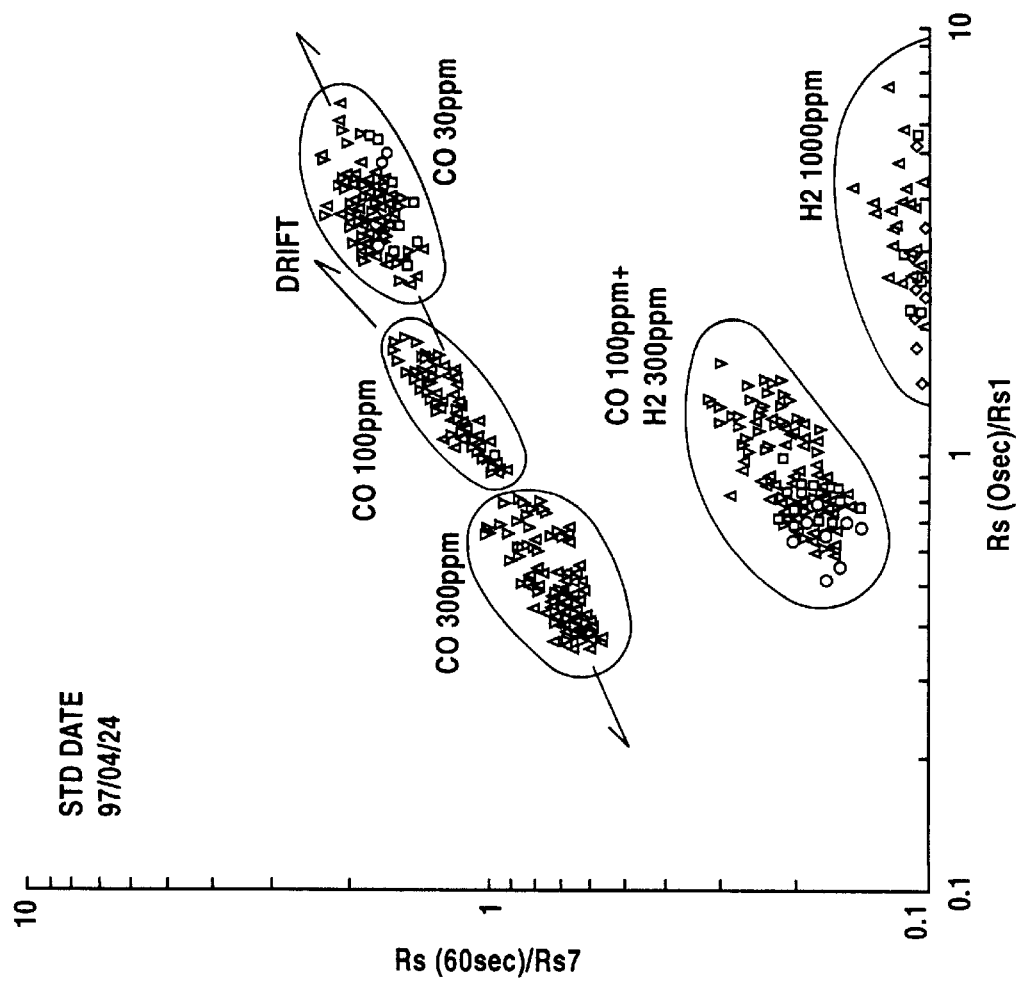
FIG. 11 is a characteristic diagram showing drift characteristics in a 0–60 sec plane in the embodiment.
Figure 12:
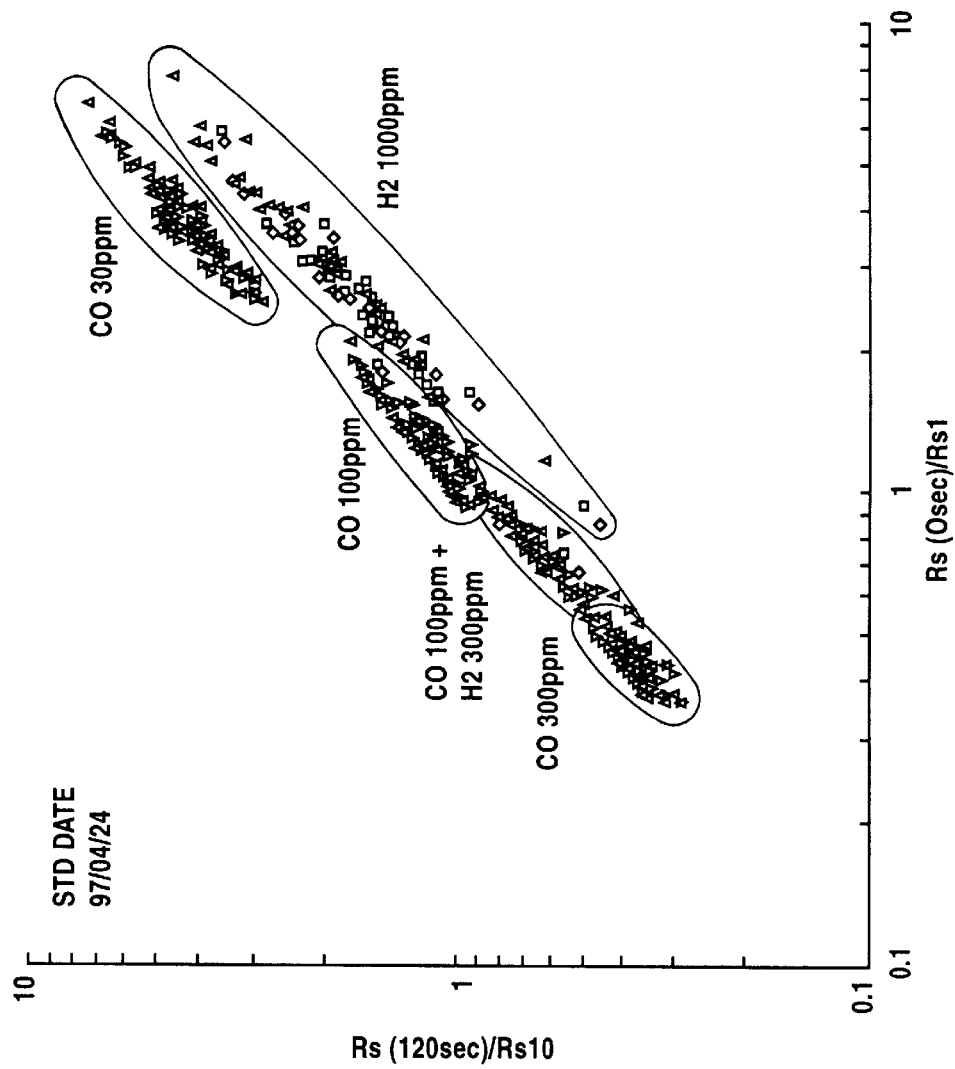
FIG. 12 is a characteristic diagram showing drift characteristics in a 0–120 sec plane in the embodiment.

In FIG. 9, a similar drift axis is present. However, the distribution of points around the drift axis is wider. This indicates that the correlation between the drift of the signals at 0th sec and the drift of the signals at the 12th sec is weaker than that of the 0th sec signals and the 6th sec signals. In the characteristic diagram of the 30th sec signals and the 0th sec signals of FIG. 10, distribution of points around the drift shaft is more extensive, and there are some points of CO 300 ppm that are hard to be distinguished from those of CO 100 ppm. In the characteristic diagram of the 60th sec signals and the 0th sec signals of FIG. 11, of points of CO 300 ppm, some points drifting most almost overlap with the standard points of CO 100 ppm. In the characteristic diagram of the 120th sec signals and the 0th sec signals of FIG. 12, as the signals at the 0th second and the signals at the 12th second are very similar to each other, the drift axis and the gas concentration axis are common, and all the topological points gather around one straight line.

Thus signals that can be used for drift compensation are those generated in the early part of the higher temperature period, for example, signals at the 4th through 20th second, and preferably, signals at the 5th through 15th second. The counterpart to be combined with is signals of the latter part of the lower temperature range, for example, signals at the 90 th through 150th second, and preferably, signals at the 120th through 150th second. In every diagram of FIG. 8 through FIG. 11, the gas concentration axis and the drift axis obliquely intersect with each other. No two axes of orthogonal coordinate system can be found to match the CO concentration and the drift. If we can get a gas concentration axis that intersects orthogonally with the drift axis, that will mean that there is an axis free of any effects of drift, and that the coordinates on that axis are determined by gas concentration alone. However, such an axis was not found.

In the embodiment, as logarithms of the sensor resistance are used, the gas concentration axis and the drift axis are straight lines. However, if the sensor resistance itself is used, the gas concentration axis will be a curved axis that is close to a parabola.

Negative Hydrogen Sensitivity

In addition to the above-mentioned data, the behavior of a mixed gas of CO 100 ppm and hydrogen 300 ppm and the behavior in hydrogen 1000 ppm are indicated in these diagrams. As can be clearly seen in FIG. 8, the sensitivity to hydrogen is slightly negative. For example, let us translate the respective points of CO 100 ppm+hydrogen 300 ppm parallel to the drift axis till getting intersection points of these points with the gas concentration axis. The resulting concentration range is from CO 80 ppm to 60 ppm. On the other hand, the distribution of points in CO 100 ppm for five weeks is narrow, and when these points are translated parallel to the drift axis, the resulting intersection points with the gas concentration axis give a distribution range of from CO 80 ppm to 120 ppm. The sensitivity to hydrogen becomes negative because the hydrogen sensitivity of the 6th second signal is higher than that of the 0th second signal. To compensate for this, a topological space comprising the 0th second signals and the 69th second signals is used.

Figure 13:
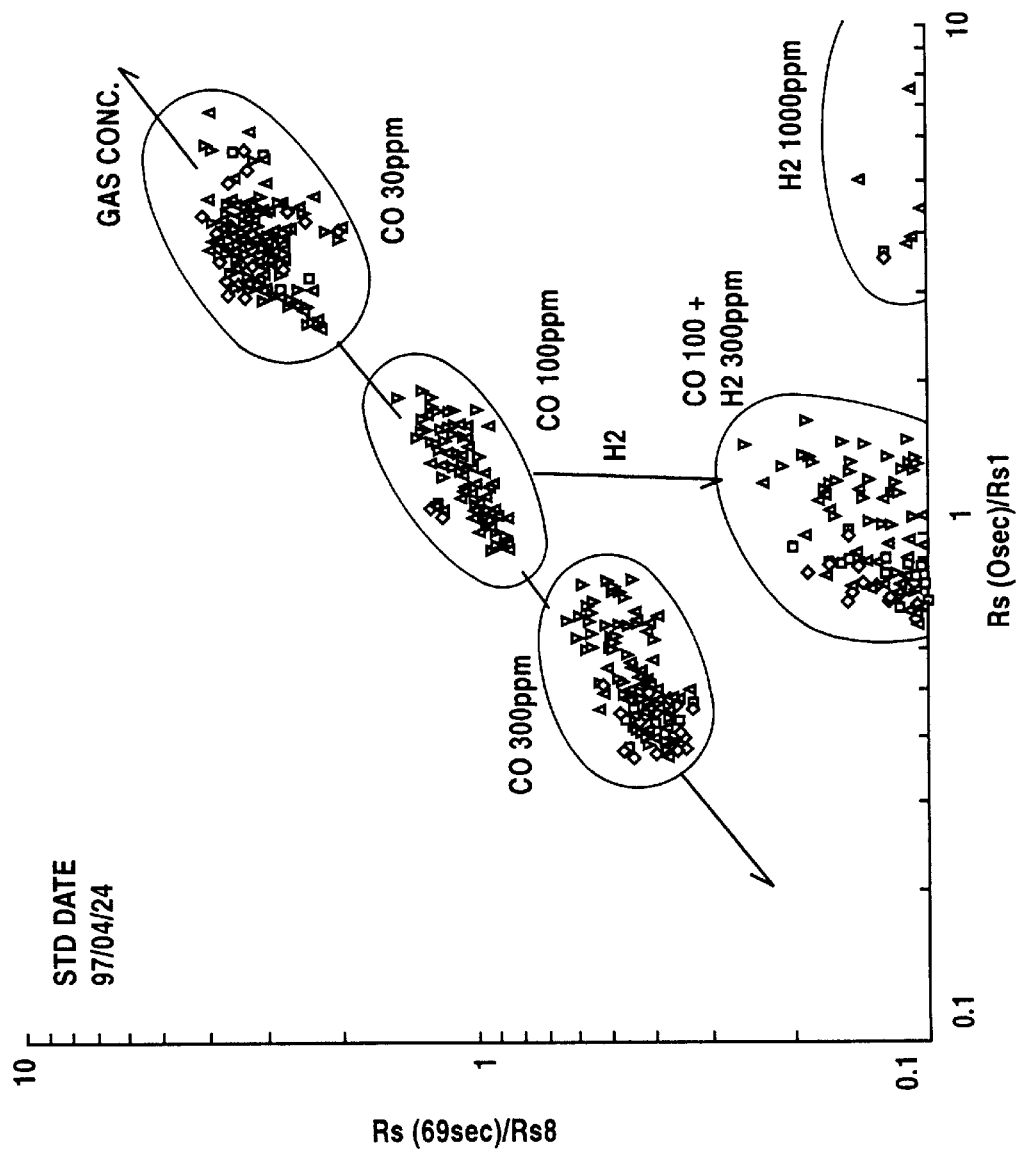
FIG. 13 is a characteristic diagram showing drift characteristics in a 0–69 sec plane in the embodiment.

Data for five weeks of this case are shown in FIG. 13. As can be clearly seen in FIG. 13, when hydrogen is present, the resistance at the 69th second decreases significantly. Thus data points are extremely away from the gas concentration axis. Hence the distance of descent from the gas concentration axis towards the bottom of FIG. 13 is used as a hydrogen detection signal.

The hydrogen detection signal is not an accurate one, and in FIG. 13 no oblique coordinate system is used. However, the negative hydrogen sensitivity is small, the signal is for its compensation, and thus we can use a hydrogen detection signal that lacks quantitativeness. In correcting the hydrogen sensitivity, two approaches may be taken. One is to restore the hydrogen sensitivity to zero, that is slightly negative in FIG. 8; in other words, to design a CO detector that is extremely selective to CO only. Another approach is to make compensation so that the CO detector's ratio of CO sensitivity to hydrogen sensitivity is 10:1, just like the intrinsic characteristic of TGS203. Choice between these two approaches is arbitrary.

Drift Compensation

Figure 14:
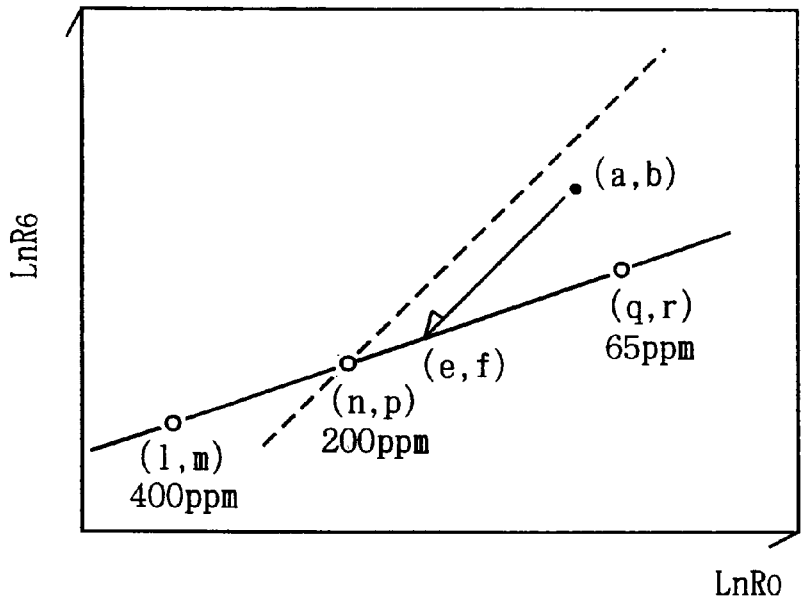
FIG. 14 is a characteristic diagram showing the mechanism of calculating CO concentration in the embodiment.

The principle of drift compensation is shown in FIG. 14. The solid line in the diagram is the gas concentration axis, and the dashed line is the drift axis. The standard signals at three points in 65 ppm, 200 ppm and 400 ppm are stored in the EEPROM 20. A point (a, b) in a topological space of two dimensions LnR0 and LnR6 is determined by measurement.

The coordinates of the respective standard signals in this topological space are defined as shown in FIG. 14. The point (a, b) is translated parallel by to the drift axis, and its intersection point with the gas concentration axis has coordinates (e, f). When coordinates (e, f) are determined, the CO concentration can be determined from the position on the gas concentration axis. Translation from coordinates (a, b) to coordinates (e, f) is a projection parallel to the drift axis onto the gas concentration axis.

The technique of projection may be arbitrary. For example, in the topological space of FIG. 14, data showing CO concentration may be written to develop a two-dimensional map. Then the CO concentration can be derived from the position on the map. If the map is rough and data directly corresponding to given coordinates are not available, the data can be obtained by interpolation between points on the map. Another method is to draw three lines parallel to the drift axis from the respective standard points (l, m), (e, f) and (q, r), and write compensation values for CO concentration on each line. The compensation value is 1 on the gas concentration axis. The compensation values are set to compensate for increase in resistance due to drift. The gas concentration axis is translated to pass the measurement point to determine intersection points with the two compensation lines on both sides. The compensation values on the respective compensation lines are determined, and the compensation value of the measurement point is interpolated. Then, with the compensation value thus obtained, the logarithm of the sensor resistance at the 0th second is compensated and converted into CO concentration. In these modifications, limitations to projection can be reflected in the compensation values of compensation lines and values on the map. Thus fine control of projection can be made with ease.

Temperature & Humidity Dependence

Figure 16:
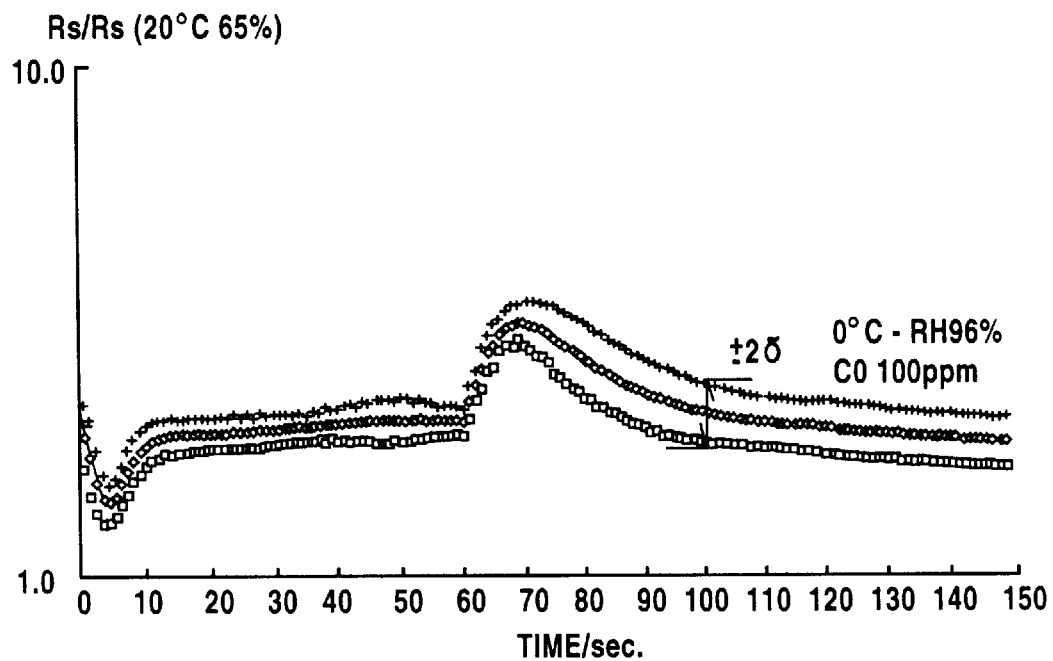
FIG. 16 is a characteristic diagram showing temperature & humidity dependence of the gas sensor between 20° C.—65% RH and 0° C.

In FIG. 16, the ratio of the resistance at 0° C. and relative humidity of about 96% and the resistance at 20° C. and relative humidity of 65% in CO 100 ppm is shown for 10 samples of TGS203. The axis of abscissa indicates timing of the temperature change. The greater part of the temperature & humidity dependence is compensated as a secondary effect of drift compensation between the 0th second and the 6th second.

Figure 17:
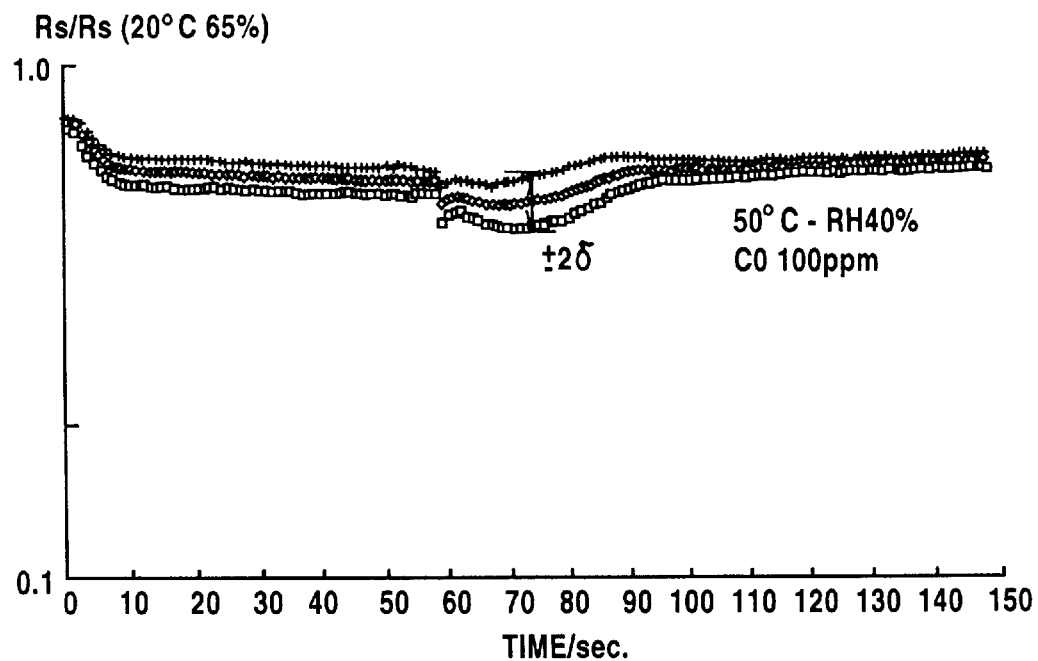
FIG. 17 is a characteristic diagram showing temperature & humidity dependence of the gas sensor between 20° C.—65% RH and 50° C.—40% RH.

In FIG. 17, the ratio of the resistance at 50° C. and relative humidity of about 40% and the resistance at 20° C. and relative humidity of 65% in CO 100 ppm is shown for the same 10 samples of TGS203. The greater part of the temperature & humidity dependence is compensated as a secondary effect of drift compensation between the 0th second and the 6th second.

Signal Processing

Figure 18:
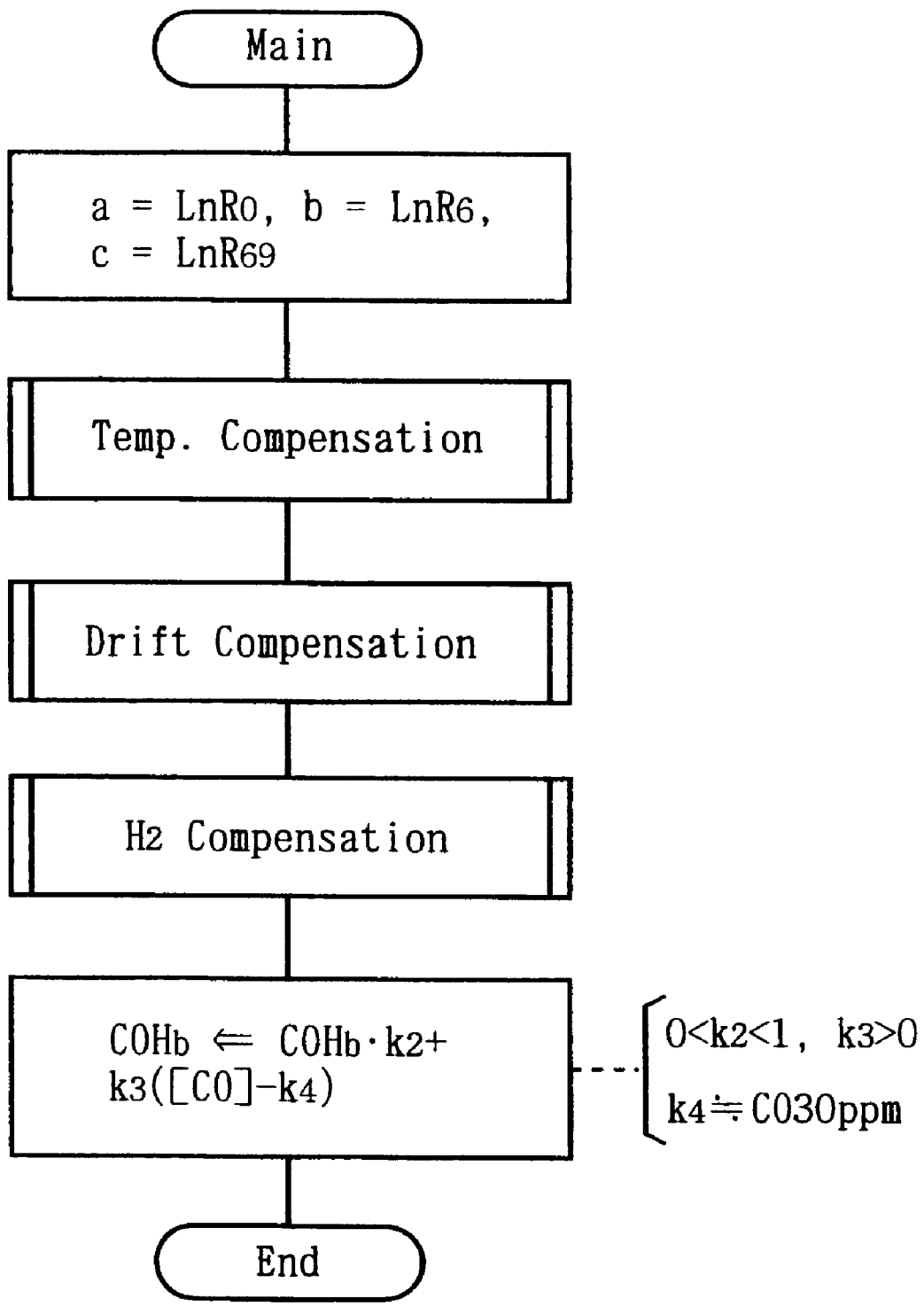
FIG. 18 is a flow chart showing the main program of the embodiment.
Figure 19:
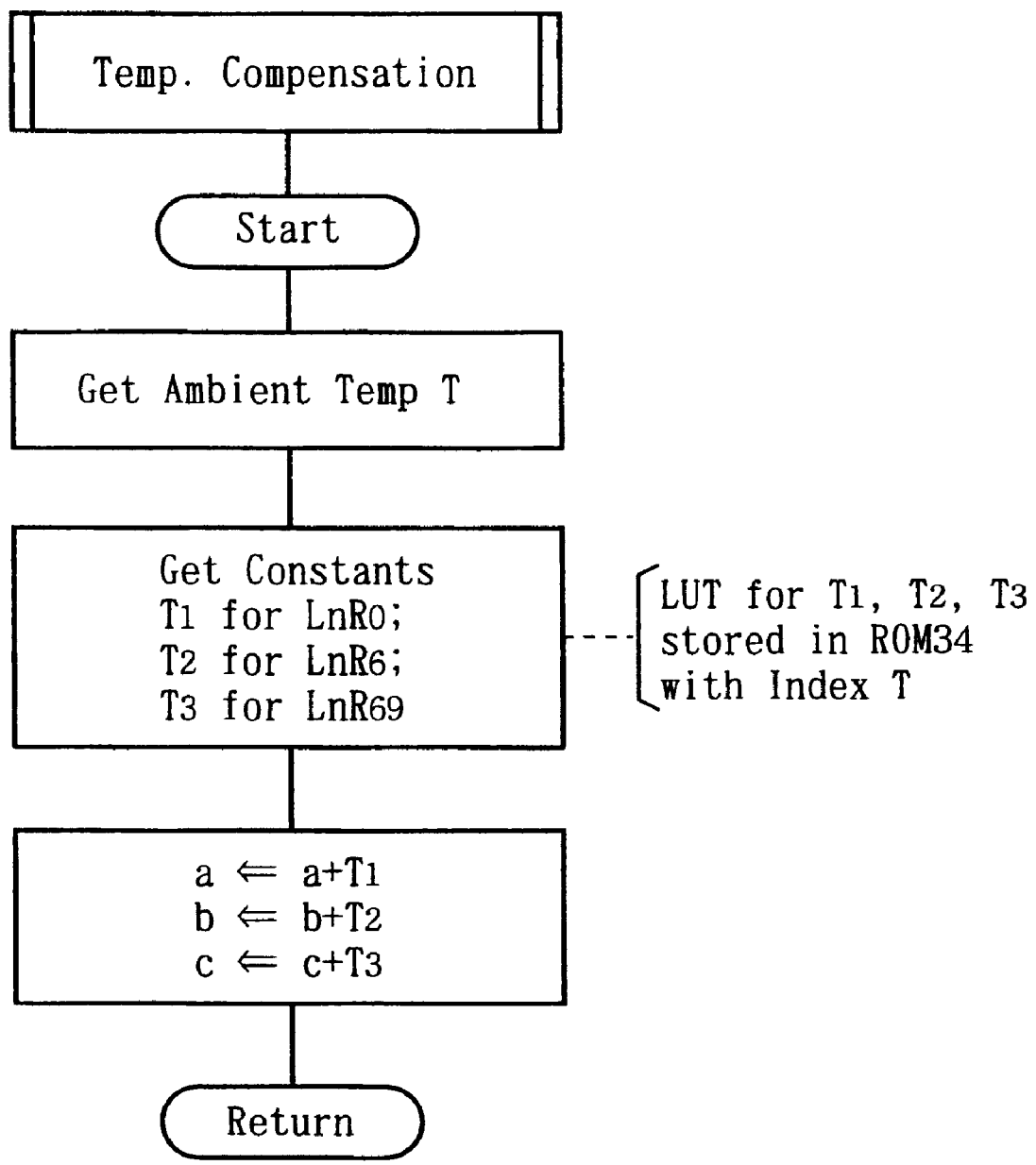
FIG. 19 is a flow chart showing temperature & humidity compensation in the embodiment.
Figure 20:
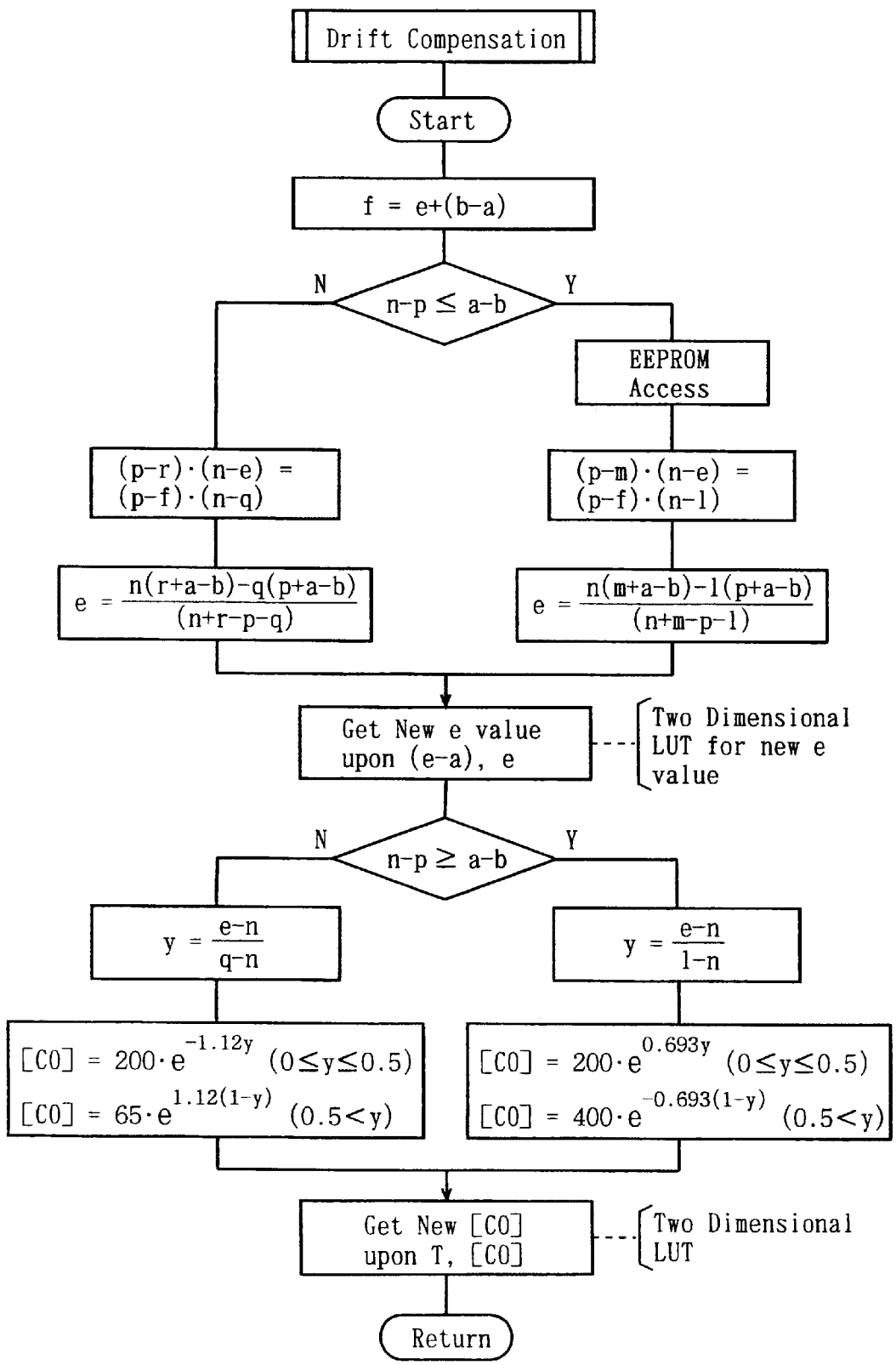
FIG. 20 is a flow chart showing drift compensation in the embodiment.
Figure 21:
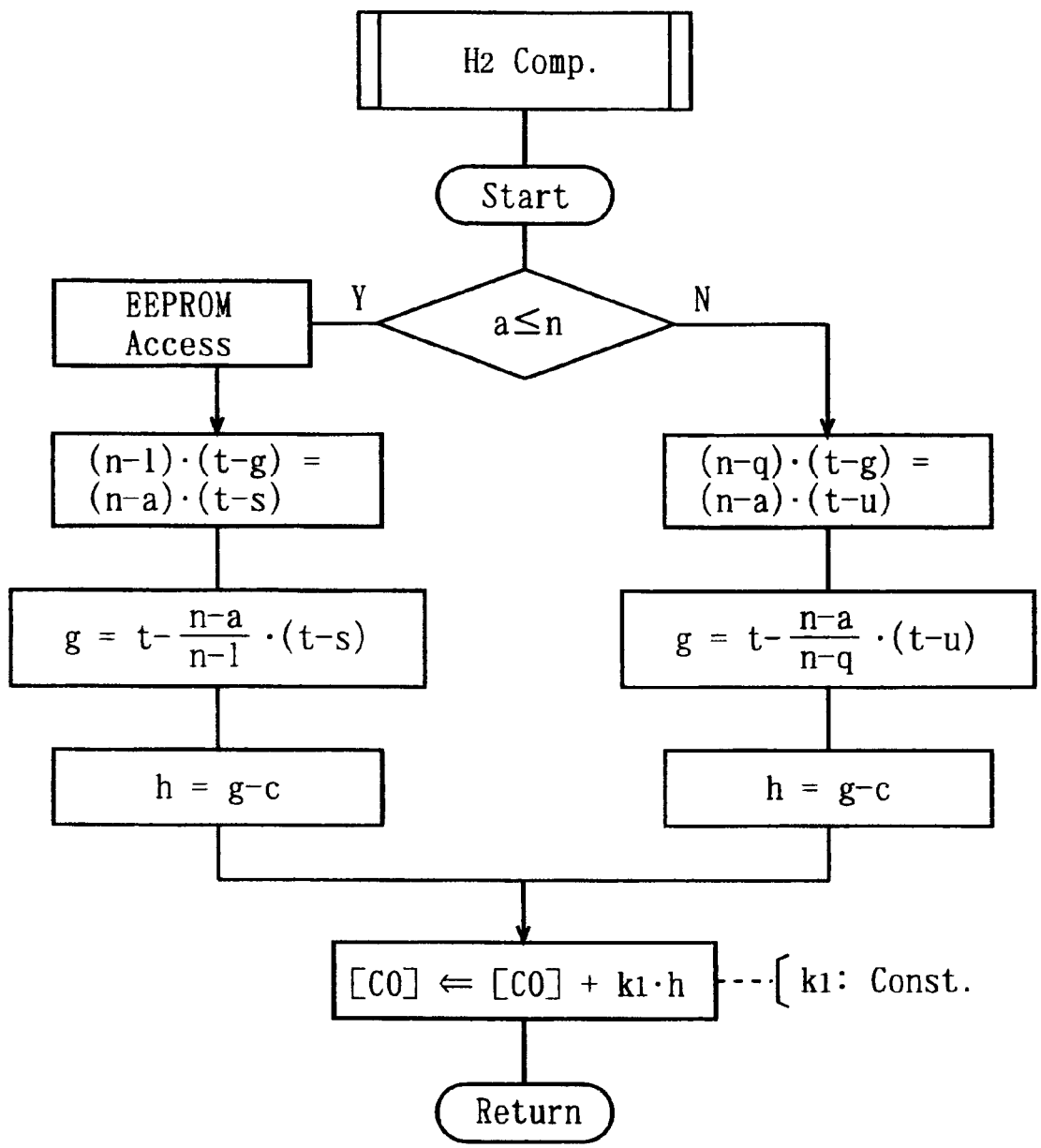
FIG. 21 is a flow chart showing compensation for coexistent hydrogen in the gas detector of the embodiment.

Calculation of CO concentration is shown in FIG. 18 through FIG. 23. FIG. 18 shows the main loop. First, three variables, a, b and c are defined by measurement data. Next, the CO concentration is determined by a subroutine of temperature compensation (FIG. 19), a subroutine of drift compensation (FIG. 20), and a subroutine of hydrogen compensation (FIG. 21). Finally, the CO hemoglobin concentration in blood is determined from the CO concentration. The initial value of COHb is set at 0 when reset. This conversion itself is well known, and k2, k3 and k4 are constants. Here k4 is a value corresponding to about CO 30 ppm that is below the lower limit of detection. Thus no detection is made when the CO concentration is 30 ppm or under.

Subroutine of Temperature Compensation

In the subroutine of temperature compensation in FIG. 19, the ambient temperature T is derived from a thermistor 42.

In a program memory 34 is stored a look-up table of compensation values T1, T2 and T3 for a, b, c based on the ambient temperature. These compensation values are read out and added to a, b and c.

Subroutine of Drift Compensation

The subroutine of drift compensation is shown in FIG. 20. The gradient of the drift axis is 1, and (e−a) equals (f−b). Hence we get f=e+(b−a). Then one of two unknowns e, f can be eliminated. Next, a check is made whether (n−p) is equal to or greater than (a−b). If this condition is not met, when the drift axis is extended from the point of 200 ppm, the measurement point is below the drift axis, and the detected concentration is 200 ppm or under. Next, the point (e, f) divides internally the segment that is defined by two standard signals of 65 ppm and 200 ppm. Hence e and f and the coordinates n, p, q, r of the standard signals of 65 ppm and 200 ppm are constrained by a single relation. Thus the coordinate e can be determined by using this relation.

Figure 22:
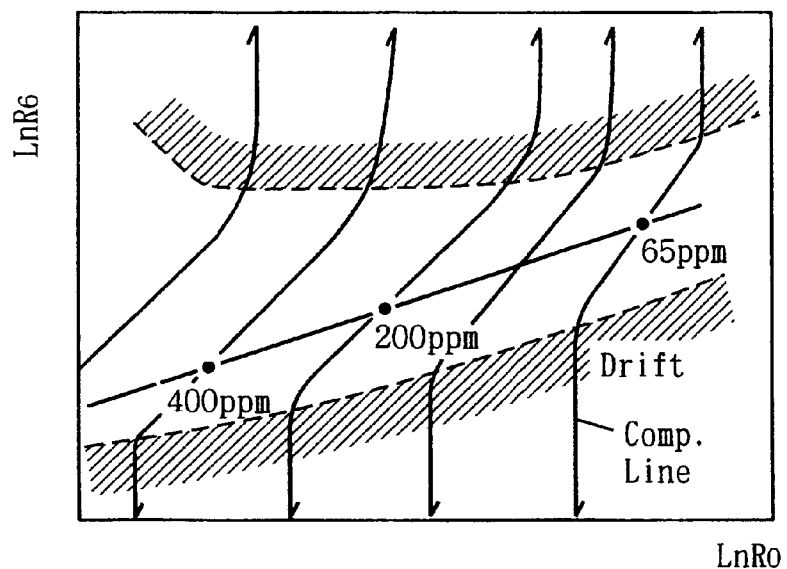
FIG. 22 is a characteristic diagram showing details of drift compensation in the embodiment.

The determined e has no constraints of projection. A point extremely away from the gas concentration axis and a point close to the axis are projected equally. Projection is symmetrical between the area above the gas concentration axis and the area below the gas concentration axis. In contrast to it, when the drift from the gas concentration axis towards higher resistance side is large, it is desirable to constrain the projection to compensate for just a part of the drift. When the drift is from the gas concentration axis towards the lower resistance side, it is desirable to make a more modest compensation than the drift to the higher resistance side. The gradient of the drift axis at about CO 30 ppm is slightly greater than the gradient of the drift axis at 100 ppm or over. It, therefore, is desirable to change the gradient of the drift axis for concentration to concentration. CO of 30 ppm is harmless and is not included in the scope of inspection. There is no need of making drift compensation for CO of such a low range of concentration. Hence, as shown in FIG. 22, it is desirable that the compensation is made asymmetrical between the area above the gas concentration axis and the area below the gas concentration axis, and that the drift is compensated for partially when the distance from the gas concentration axis is large.

When a map is used or when plural drift axes are prepared for various concentrations, the above-mentioned processing can be done by handling data in the map or by handling gradients of the drift axes. However, in the present embodiment, the above-mentioned processing is done by means of a two-dimensional look-up table stored in a program memory 34 after e is determined. The indices of this look-up table are (e−a) and e. (e−a) is proportional to the distance from the gas concentration axis. The sign of (e−a) is reversed across the gas concentration axis. The value of e indicates the CO concentration, and selection between processing of lower concentration range and processing of higher concentration range is indicated by the value of e. Hence the value of e is replaced by means of the look-up table according to (e−a) and e. In this way, one can make compensation asymmetrical about the gas concentration axis. This compensation is modest in an area where the distance from the gas concentration axis is great, and the compensation is modest in the lower concentration range. The processing corresponding to FIG. 22 is not needed.

When the value e is determined finally, the next step is to determine the internal ratio y of the segment between 65 ppm and 200 ppm. When y is 0, the CO concentration is 200 ppm. When y is 1, the CO concentration is 65 ppm. The concentration varies along the segment in a range about three times as large as the minimum. If this is solved directly, the series expansion of exp(y) will require terms of the second degree or over. Hence we assume a midpoint between 65 ppm and 200 ppm. For any point from the midpoint and towards 200 ppm, series expansion is based on the concentration of 200 ppm. For any point from the midpoint and towards 65 ppm, series expansion is based on the concentration of 65 ppm. With this arrangement, approximation by exp (y)=1+y hardly generates approximation errors. In this way, the CO concentration before hydrogen concentration compensation is determined.

Now, when the obtained topological point is above the drift axis that passes CO 200 ppm, the CO concentration exceeds 200 ppm. In this case, the EEPROM is accessed, and the standard signal of CO 400 ppm is read out. Then the CO concentration is determined in a similar manner. The processing in this case is similar to the processing using two standard signals of CO 65 ppm and 200 ppm. The standard signal of CO 400 ppm is used in place of the standard signal of CO 65 ppm.

Figure 23:
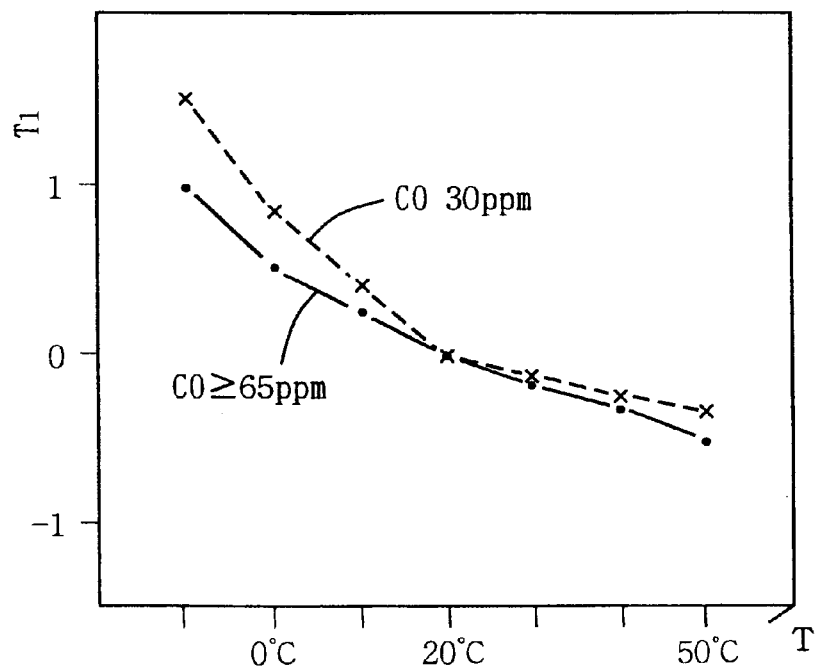
FIG. 23 is a characteristic diagram showing details of temperature & humidity compensation in the embodiment.

The temperature & humidity dependence has such a gas concentration dependence as shown in FIG. 23. The temperature & humidity dependence in the lower concentration area differs from that in the higher concentration area. However, in the stage of the subroutine of temperature & humidity compensation, the CO concentration is not known yet. Hence the CO concentration is determined tentatively, and the ambient temperature T and the tentatively determined CO concentration are used to get data from a two-dimensional look-up table stored in the program memory 34, and in turn, correct the CO concentration again. This technique neglects the CO concentration dependence of the temperature & humidity dependence, makes a first approximation, and uses the tentative CO concentration thus obtained to correct the CO concentration dependence of the temperature & humidity dependence again. The tentative CO concentration and the ambient temperature are used as the indices of the look-up table, and increments and decrements of CO concentration are stored in the look-up table. This value is added to redetermine the CO concentration. The processing corresponding to FIG. 23 can be omitted.

Subroutine of Hydrogen Compensation

Figure 15:
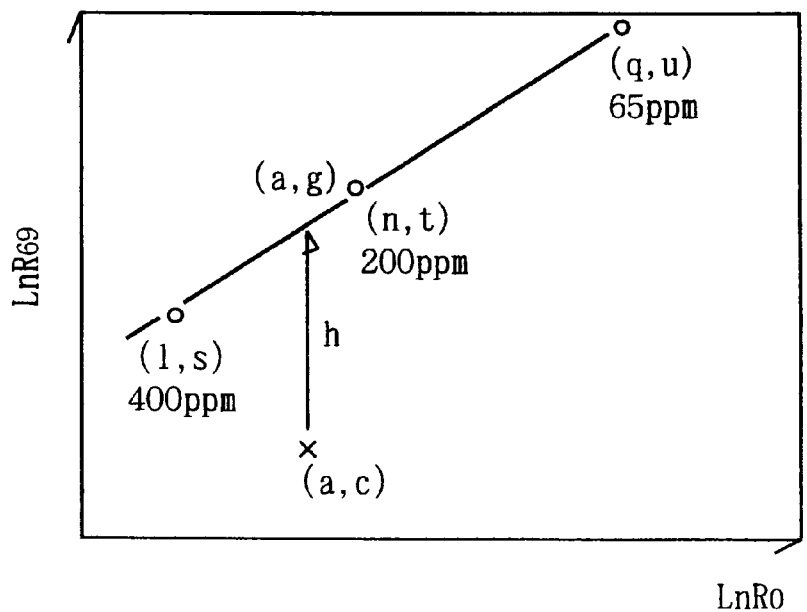
FIG. 15 is a characteristic diagram showing hydrogen compensation in the embodiment.

When the CO concentration is determined, the next step is hydrogen compensation. Its processing is shown in FIG. 21, and the principle is shown in FIG. 15. Coordinates of a measuring point are assumed to be (a, c) in a two-dimensional topological space that is defined by the logarithm of the resistance at the 0th second and the logarithm of the resistance at the 69th second. The point is vertically translated in FIG. 15 to intersect the gas concentration axis of 65 ppm, 200 ppm and 400 ppm. The coordinates of the intersection point are expressed by (a, g). The difference between g and c is h. It is assumed that the hydrogen concentration is determined by h. In this case, it is judged whether the signal of 400 ppm is needed as a standard signal by checking whether the value of a exceeds n or not. When a is n or under, the EEPROM 20 is accessed to read out the standard signal of 400 ppm. As the point (a, g) is on a segment that connects the standard signal of 200 ppm and the standard signal of 400 ppm, one expression concerning the coordinate g is generated. g can be determined from this expression. When g is determined, then h can be determined. For example, k1×h is added to the CO concentration determined by the main loop of FIG. 12. k1 is an appropriate positive constant. The standard or criterion of this addition is, for example, to null the hydrogen concentration dependence of the CO detector or to set the ratio of CO sensitivity and hydrogen sensitivity at an appropriate value such as 10:1. When a is greater than n or the point (a, c) that is determined in FIG. 15 is on the right of the standard signal of 200 ppm, the standard signals of 65 ppm and 200 ppm are used. Then h is determined in a manner similar to that mentioned above to make hydrogen concentration compensation.

Modification

Figure 24:
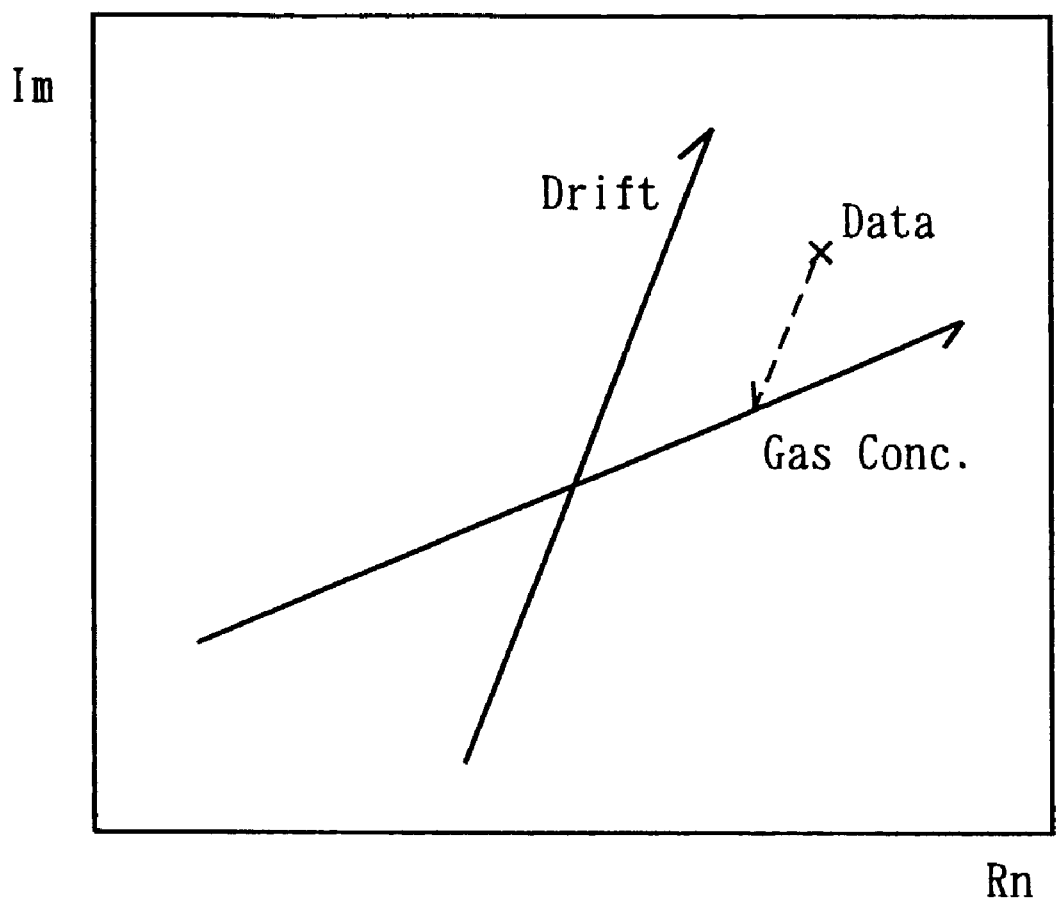
FIG. 24 is a characteristic diagram showing an oblique coordinate system two-dimensional topological space in a modification using Fourier transformation.

A processing using Fourier transformation is shown in FIG. 24. Fourier transformation is given to the logarithm of a sensor signal generated in the course of the temperature change. Then, a component that has a high correlation with the target gas concentration is selected from the transform. This selected component must have a high correlation with noises such as drift, temperature & humidity dependence, and interference gases, and a low dependence on the target gas. When a two-dimensional topological space of the Fourier transform component is determined, it will be, for example, just as shown in FIG. 24. Here again, the gas concentration axis and the noise axis do not intersect orthogonally with each other. When they are treated as a two-dimensional oblique coordinate system, noise is compensated for just in the same manner as the embodiment, and the target gas concentration can be calculated with high overall accuracy.

Sensor Temperature

Figure 25:
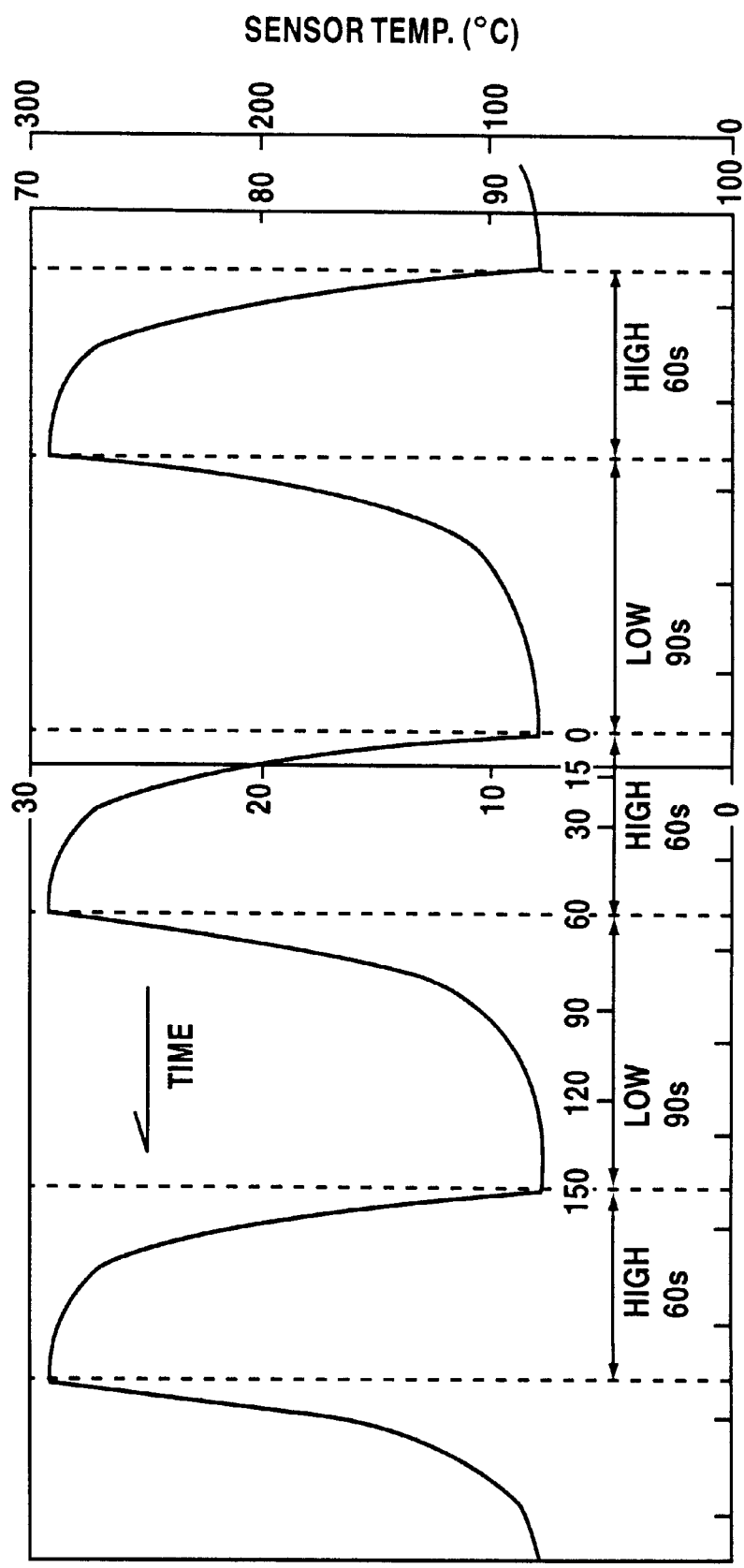
FIG. 25 is a characteristic diagram showing the relationship between the operation period of the gas sensor used in the embodiment and the sensor temperature.

For your reference, FIG. 25 shows how the temperature of the gas sensor used in the embodiment varies in the higher temperature range and the lower temperature range.

Best embodiment

Figure 26:
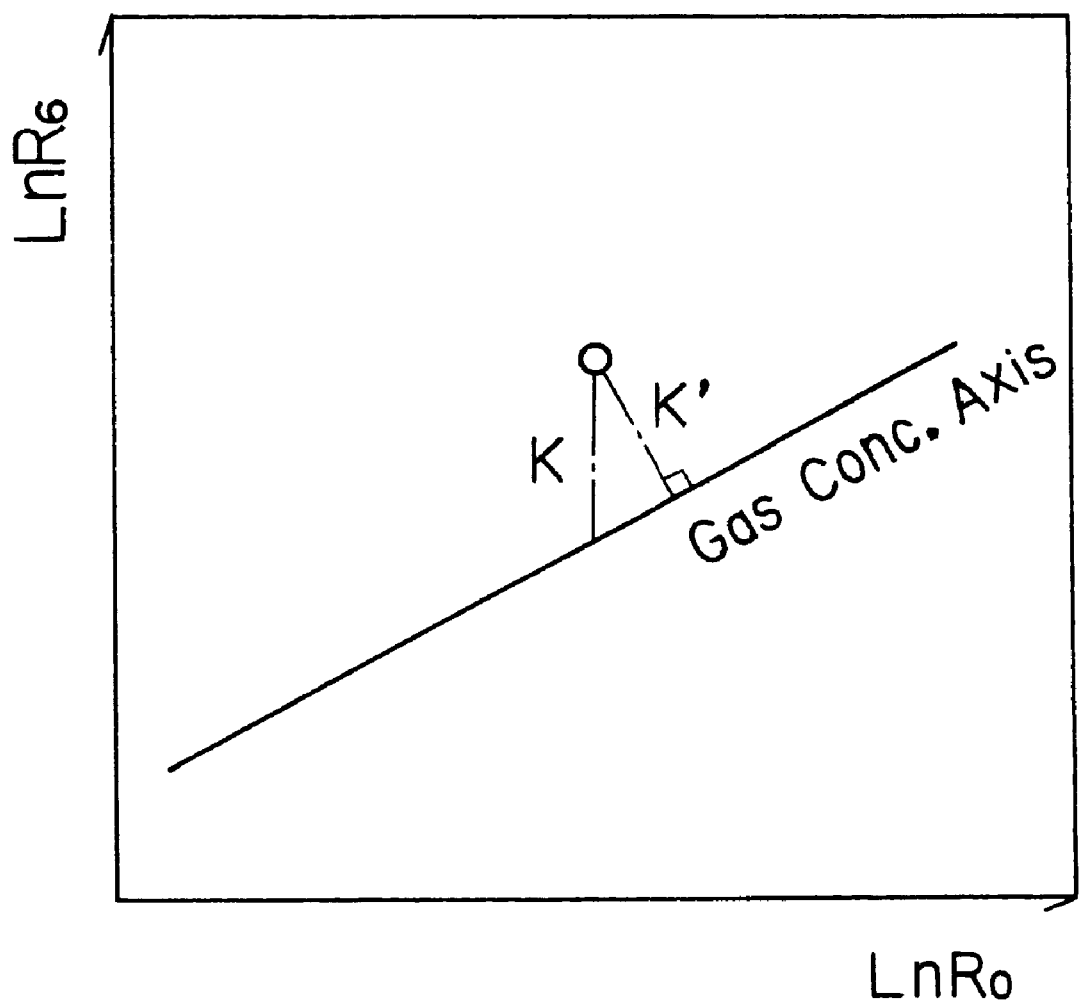
FIG. 26 is a characteristic diagram showing the principle of operation of a most preferred embodiment.

A most preferred embodiment is shown in FIG. 26 and subsequent diagrams. The gas sensor used is TGS203. Data are shown as mean values of 40 to 60 samples of the sensor. When an upper mark and a lower mark are indicated, they represent the maximum and the minimum of the data distribution. As the construction, etc. of the gas detector are common to those of the above-mentioned embodiment, only differences between them will be described.

The principle of the most preferred embodiment is shown in FIG. 26. The axis of abscissa is LnR0 (the logarithm of the resistance at the 0th second), and the axis of ordinate is LnR6 (the logarithm of the resistance at the 6th second). When the gas concentration is changed in a constant atmosphere, a gas concentration axis will be obtained in the topological space. A constant atmosphere may be, for example, 20° C. and relative humidity of 40%. The gas concentration range is, for example, from CO 30 ppm to 600 ppm. LnR0 and LnR6 form a two-dimensional topological space. In place of such a topological space, the axis of ordinate and the axis of abscissa may be axes of linear combination of plural sensor signals, respectively. The essential thing is to provide a topological space derived from the temperature waveform of the gas sensor. Now, if the sensor does not change from its initial state, any interference gases such as hydrogen are not present, and the ambient temperature, on ambient humidity, etc. does not change, the sensor signals will remain on the gas concentration axis. If a factor of disturbance such as drift or change in humidity is added, the topological point will shift from the gas concentration axis as shown by ○ in the diagram. The magnitude of this shift K or K' indicates the magnitude of disturbance. In the case of FIG. 26, presence of the topological point above the gas concentration axis indicates increase in resistance due to drift or due to decrease in relative humidity. Presence of the point below the gas concentration axis indicates decrease in resistance due to reverse drift on due to increase in relative humidity, etc. Hence the direction of compensation above the gas concentration axis is opposite to that below the axis, it is preferable and the magnitude of compensation according to the distance from the gas concentration axis above the gas concentration axis differ from that below the axis. In the embodiment, a relatively strong compensation is given above the gas concentration axis, and a relatively weak compensation is given below the gas concentration axis.

In this way, the first step of compensation is to define a topological space derived from the temperature change of the gas sensor. This topological space may be a two-dimensional space using signals at two different timings on the temperature waveform, a space of more higher dimensions with more points, a space using a linear combination of sensor signals at plural timings for each dimension, a space using Fourier transform of the temperature waveform for each dimension, etc.

In such a topological space, there is a gas concentration axis generated when, in a constant atmosphere, for example, under conditions close to a constant temperature and a constant humidity, the gas concentration is changed. A deviation from the gas concentration axis indicates the strength of disturbance to the gas sensor. The magnitude of compensation is determined by the distance from the gas concentration axis, and the magnitude of compensation should be changed according to in which direction the deviation occurs from the gas concentration axis (in the case of the diagram, above or below).

One difference from the embodiment is that compensation is discrete rather than analogous. In the former embodiment, it was intended to detect CO with an accuracy of ±20%. Such an accuracy is an over-specification for a CO alarm. Hence 0.7 (high humidity), 1 (no compensation), 1.4 (a little low humidity), 2 (low humidity), and 3 (low humidity and drift) are used as compensation constant L to compensate the CO concentration by 40% between the steps. In this compensation, constants L are determined so that priority is given to compensation for relative humidity and compensation for drift is about one half thereof.

Figure 27:
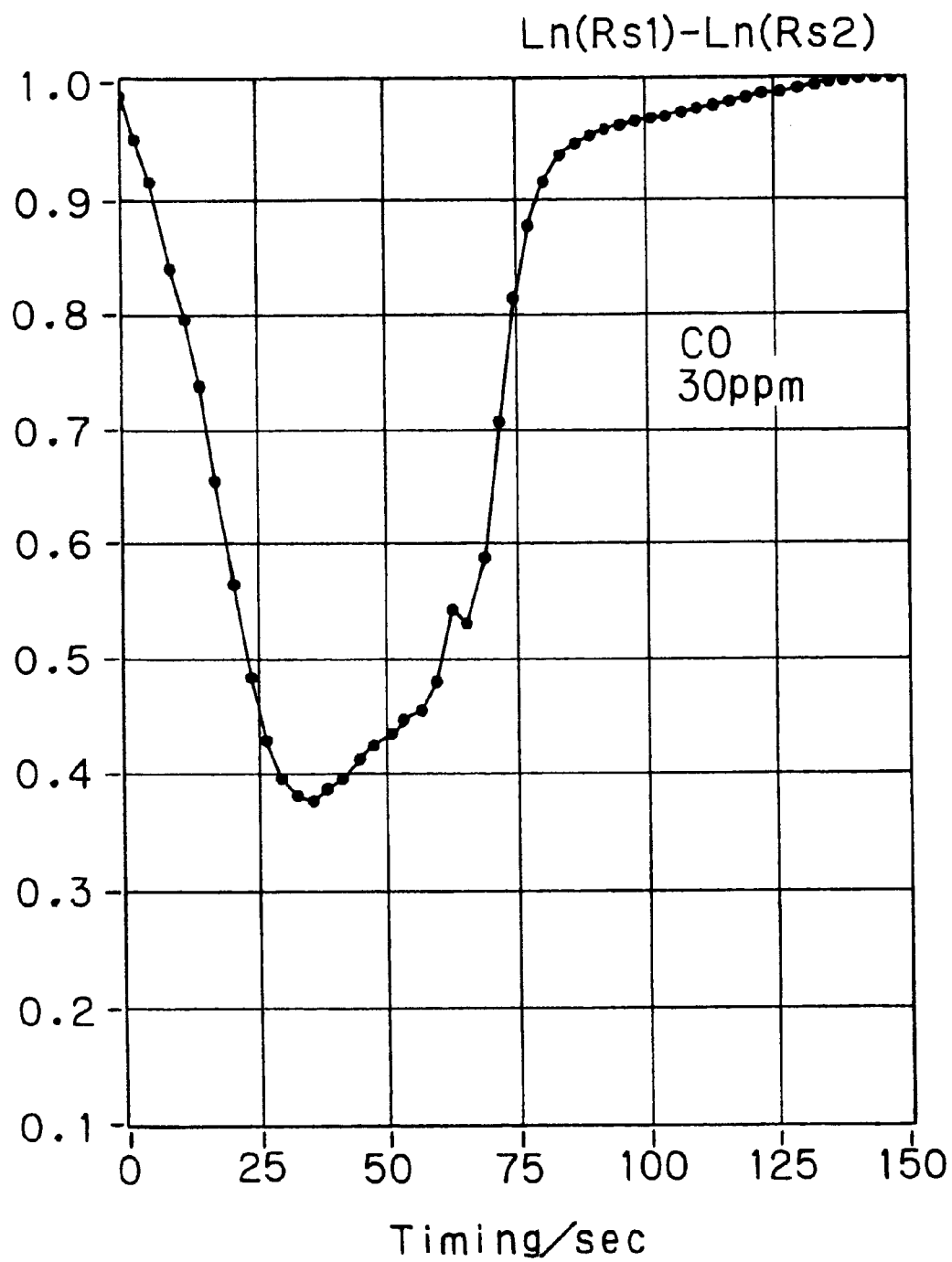
FIG. 27 is a characteristic diagram showing the correlation concerning relative humidity dependence of the gas sensor used in the embodiment. The gas concentration is CO 30 ppm, and the atmospheres are 25° C., 40% RH and 25° C., 15% RH. The diagram shows correlation of humidity dependence at the respective timings to humidity dependence at the 0th second.
Figure 28:
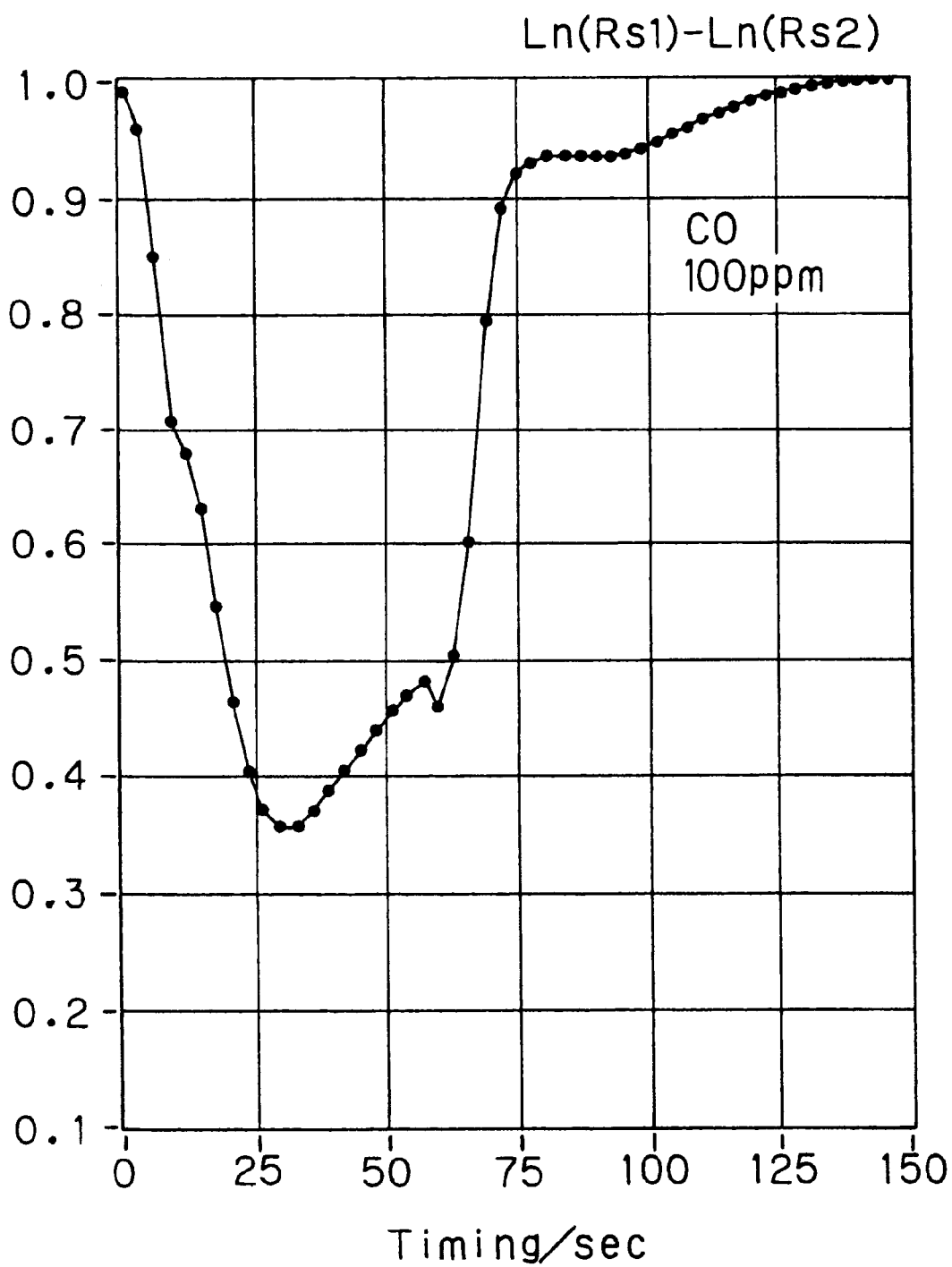
FIG. 28 is a characteristic diagram showing the correlation concerning relative humidity dependence of the gas sensor used in the embodiment. The gas concentration is CO 100 ppm, and the atmospheres are 25° C., 40% RH and 25° C., 15% RH. The diagram shows correlation of humidity dependence at the respective timings to humidity dependence at the 0th second.
Figure 29:
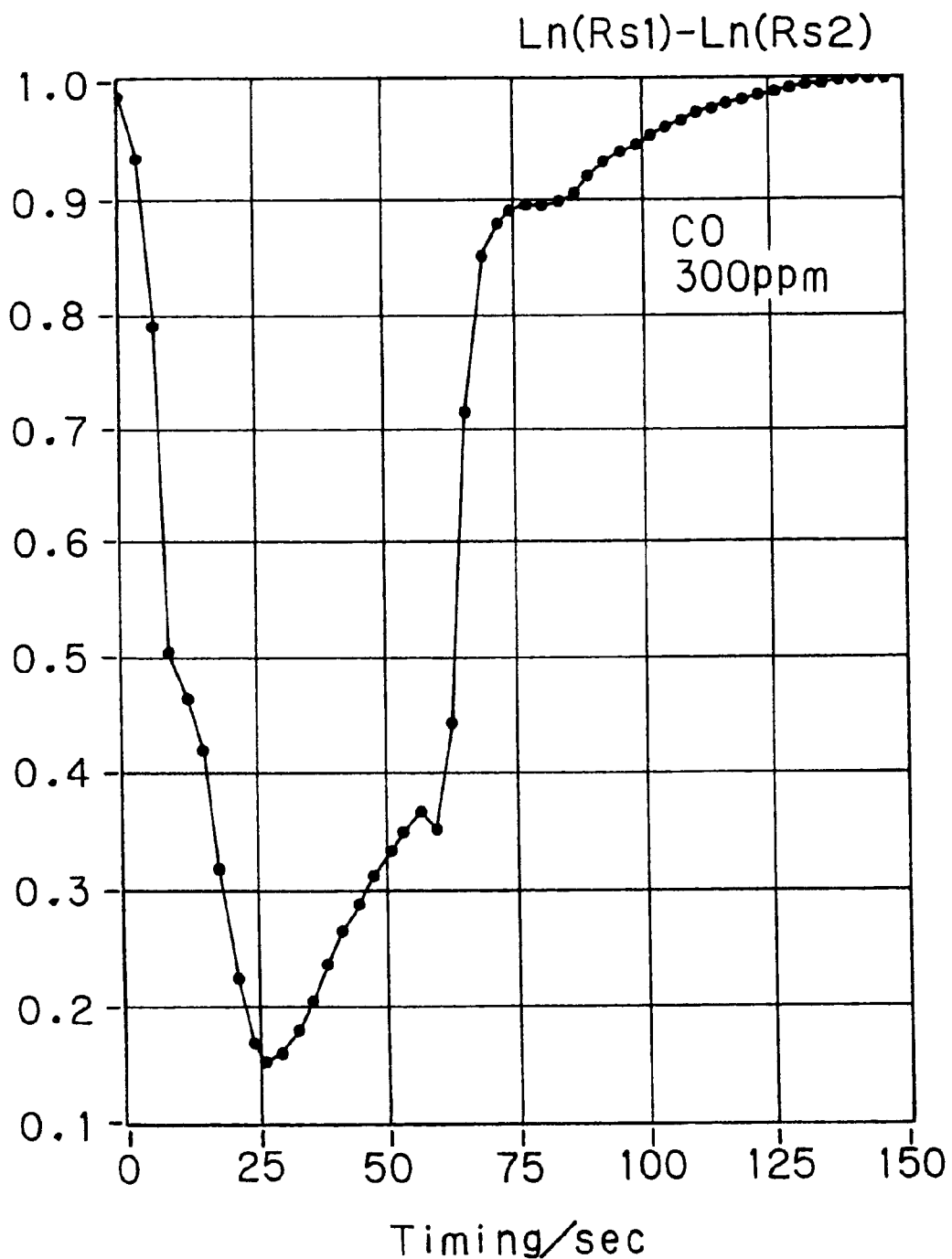
FIG. 29 is a characteristic diagram showing the correlation concerning relative humidity dependence of the gas sensor used in the embodiment. The gas concentration is CO 300 ppm, and the atmospheres are 25° C., 40% RH and 25° C., 15% RH. The diagram shows correlation of humidity dependence at the respective timings to humidity dependence at the 0th second.
Figure 30:
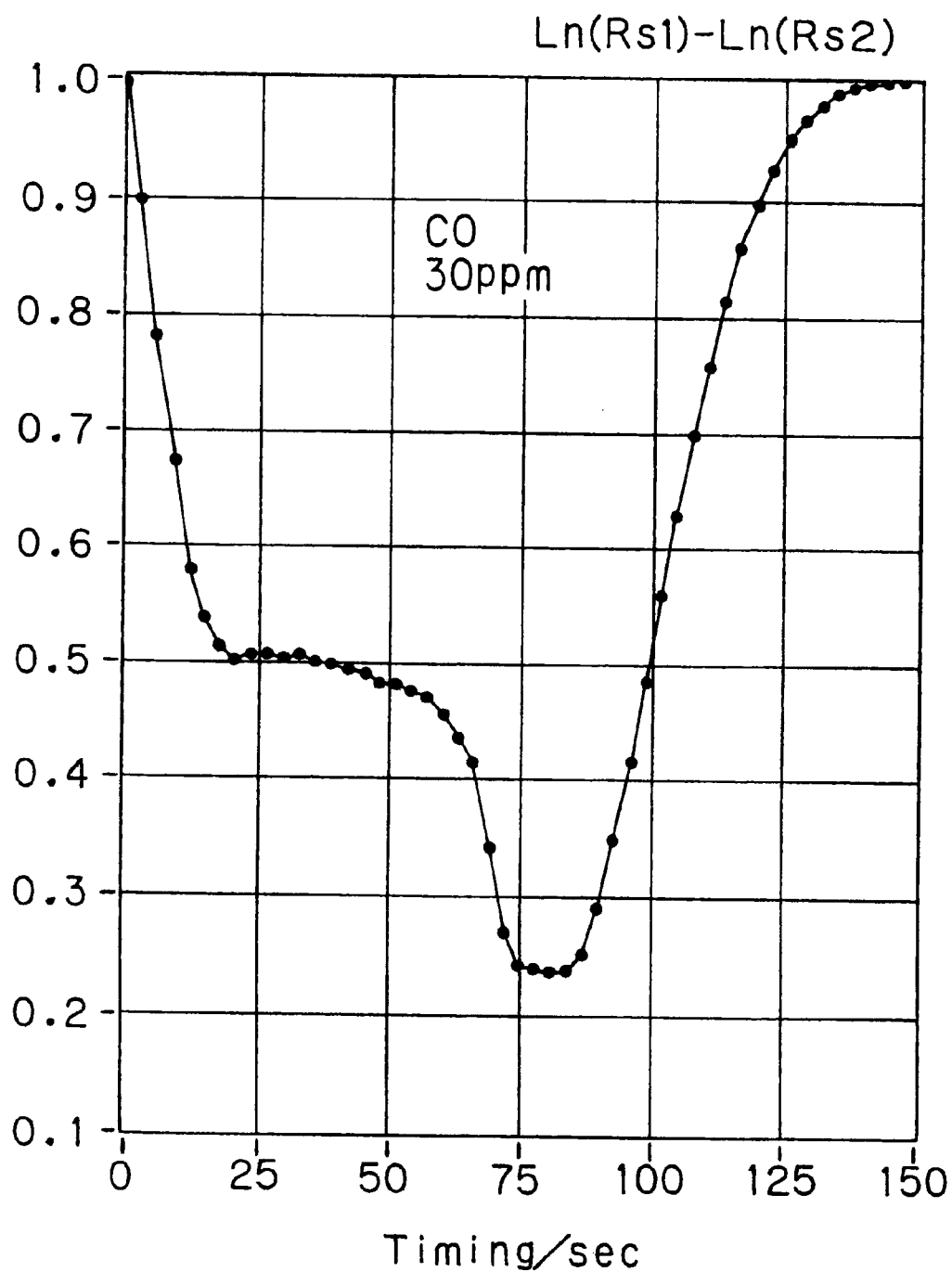
FIG. 30 is a diagram showing the correlation of relative humidity dependence of the gas sensor used in the embodiment. The gas concentration is CO 30 ppm, and the atmospheres are 25° C., 40% RH and 25° C., 95% RH. The diagram shows correlation between humidity dependence at the 0th second and humidity dependence at the respective timings.
Figure 31:
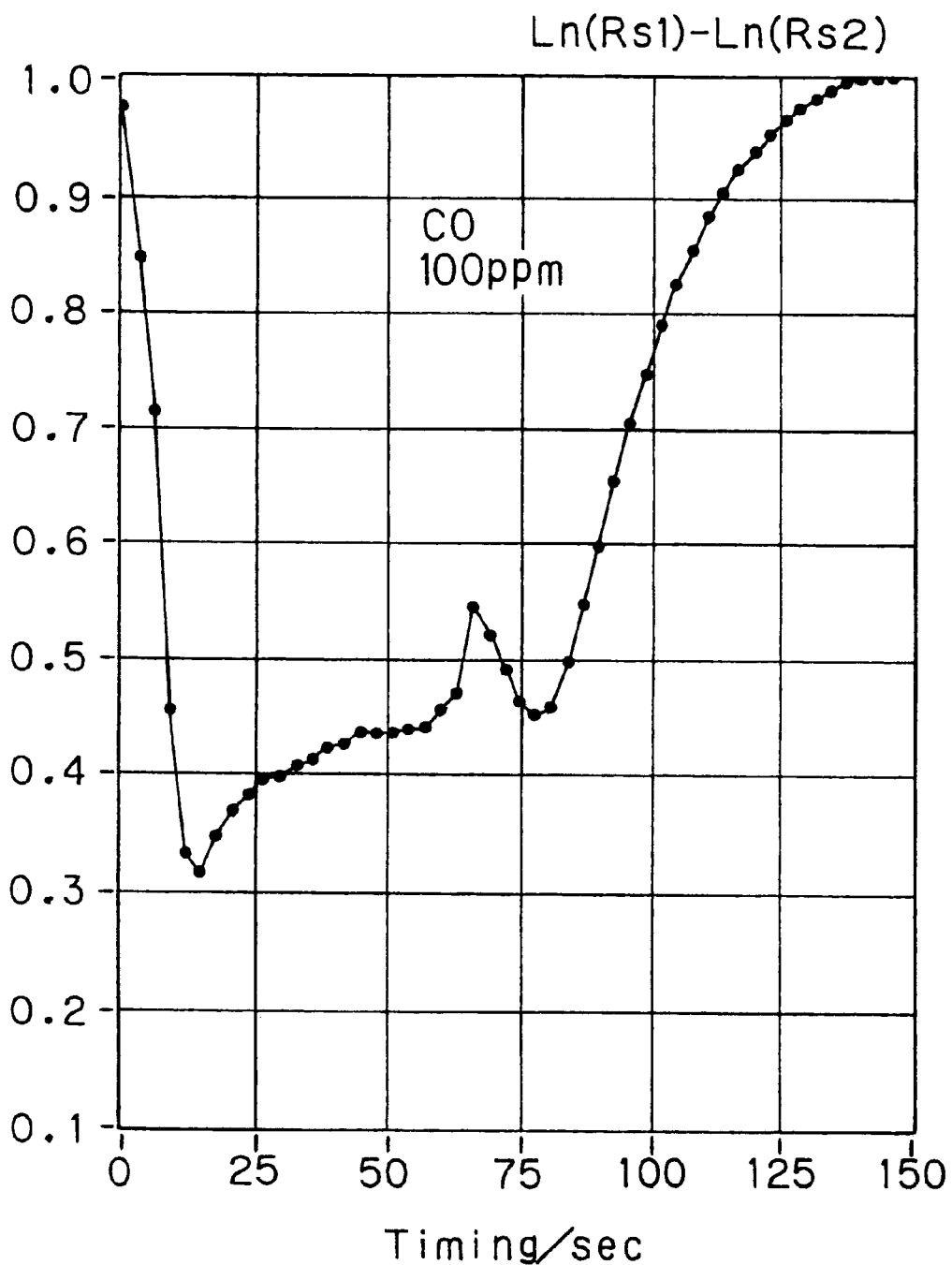
FIG. 31 is a diagram showing the correlation of relative humidity dependence of the gas sensor used in the embodiment. The gas concentration is CO 100 ppm, and the atmospheres are 25° C., 40% RH and 25° C., 95% RH. The diagram shows correlation between humidity dependence at the 0th second and humidity dependence at the respective timings.
Figure 32:
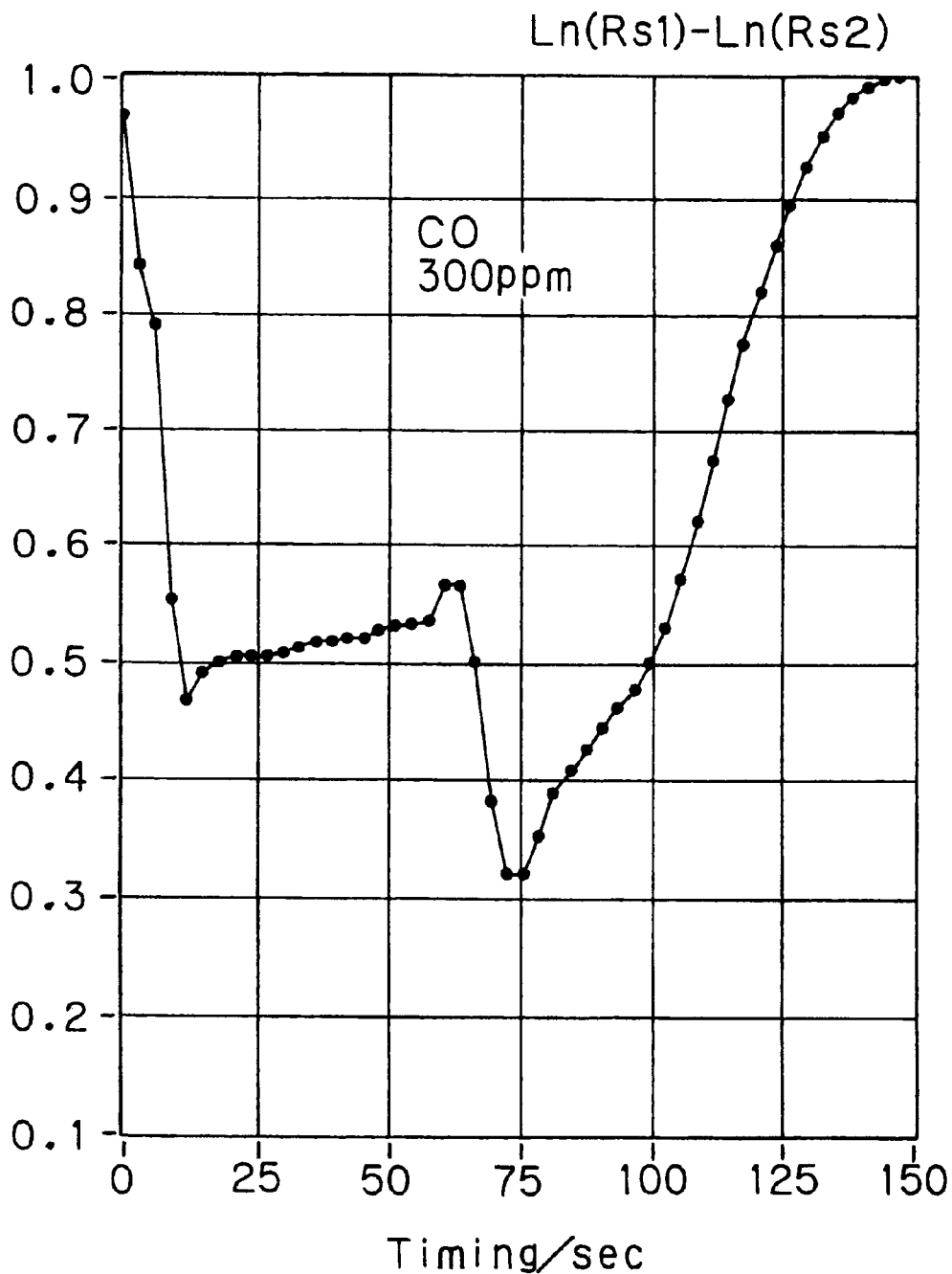
FIG. 32 is a diagram showing the correlation of relative humidity dependence of the gas sensor used in the embodiment. The gas concentration is CO 300 ppm, and the atmospheres are 25° C., 40% RH and 25° C., 95% RH. The diagram shows correlation between humidity dependence at the 0th second and humidity dependence at the respective timings.

In FIG. 27 through FIG. 29, are shown correlations of changes in resistance accompanying a drop in humidity from 25° C., 40% RH to 25° C., 15% RH. FIG. 27 shows the results of CO 30 ppm. FIG. 28 shows the results of CO 100 ppm. FIG. 29 shows the results of CO 300 ppm. The number of samples is 40. These results indicate correlation between humidity dependence at the 0th second (LnR0) and humidity dependence at other timings. As can be seen clearly from the diagrams, in the stable state of the lower temperature period from the 90 th second to 150th second, correlation of humidity dependence is very high. However, these signals are similar with each other in nature, and can not be used for compensation. In the early part of the higher temperature period, for example, at LnR6, a high correlation of 80~90% is obtained, and the correlation coefficient decreases towards the stable period of the higher temperature period. From this, we can see that with a combination of LnR0 and LnR6, relative humidity dependence can be compensated. In FIG. 30 through FIG. 32, correlations of relative humidity dependence between 25° C., 40% RH and 25° C., 95% RH are indicated. The characteristics of the signals are similar to those of FIG. 27 through FIG. 29.

Figure 33:
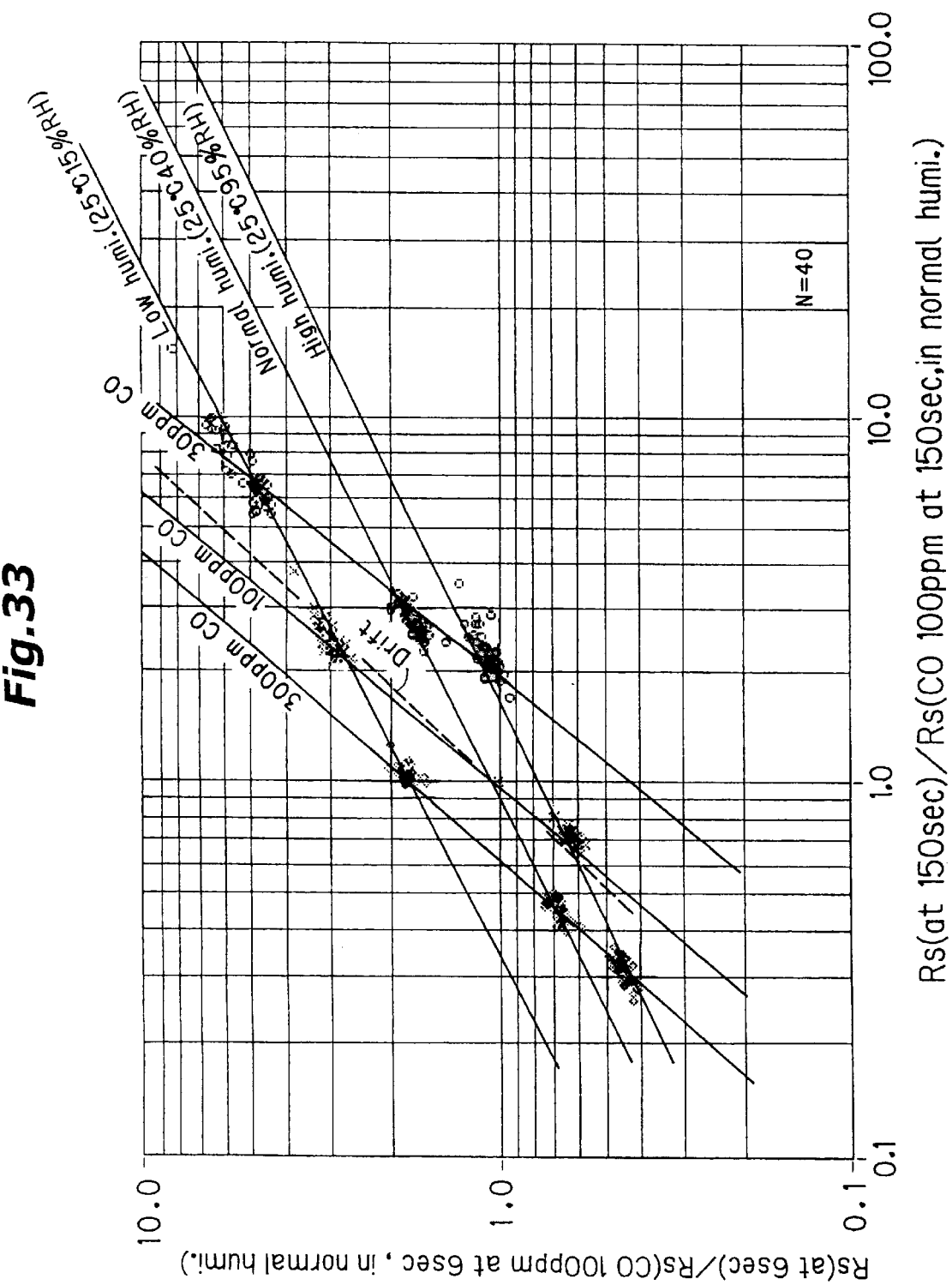
FIG. 33 is a scatter diagram showing relative humidity dependence of the gas sensor used in the embodiment. The diagram shows distributions of outputs in CO 30 ppm, CO 100 ppm and CO 300 ppm when the temperature is 25° C. and the relative humidity is changed to three kinds, 15% RH, 40% RH and 95% RH. The number of samples is 40.

FIG. 33 is a scattering chart of the results of FIG. 27 through FIG. 32. Three straight lines of smaller gradients are lines showing the influence of gas concentrations under constant temperature and constant humidity; parallel to the gas concentration axis. The lines of greater gradients are lines showing the influence of humidities at constant gas concentrations (humidity axes). The dashed line in the diagram is the line of drift. The humidity lines and the drift line are similar, but their gradients are a little different from each other.

Figure 34:
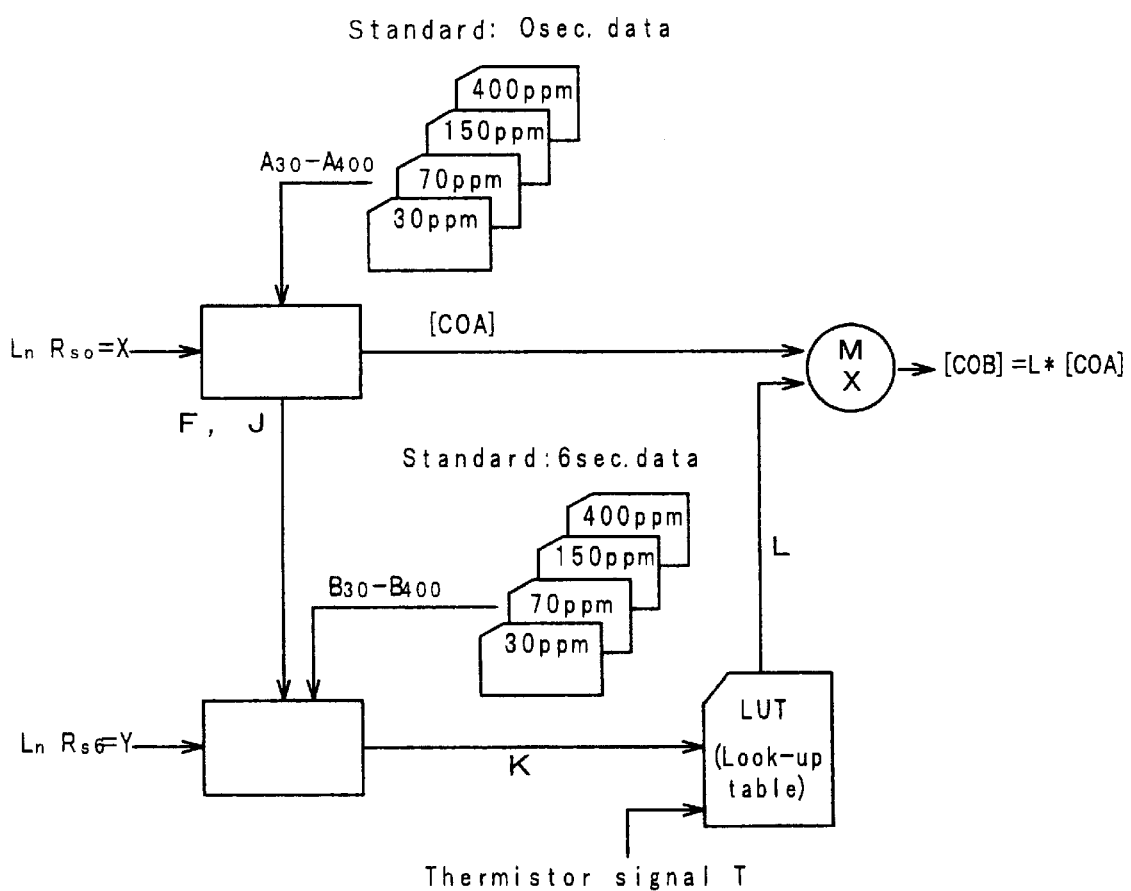
FIG. 34 is a diagram showing the flow of data in the most preferred embodiment.

The flow of data in the most preferred embodiment is shown in FIG. 34. In an EEPROM 20, are stored values of LnR0 in CO 30 ppm, 70 ppm 150 ppm and 400 ppm (A30–A400) and values of data at the 6th second, LnR6 in the same concentrations (B30–B400). The measured value of the logarithm of the sensor resistance at the 0th second is shown as X, and the measured value of the logarithm of the sensor resistance at the 6th second is shown as Y. When X is obtained, a CO concentration without compensation [COA] can be obtained by using A30–A400. A30–A400 and B30–B400 determine the gas concentration axis of FIG. 26, and when X and Y are obtained, the distance K from the gas concentration axis can be obtained. Then the look-up table is used to determine the compensation signal L for gas concentration. When the ambient temperature is changed, the thermistor signal T is inputted in the look-up table, a two-dimensional look-up table with indices K and T. In the embodiment, however, for simplicity, the processing of thermistor signal T is omitted. The compensation constant L obtained is multiplied with the CO concentration without compensation [COA], and the product [COB] is used as the output CO concentration.

Figures 35, 36:
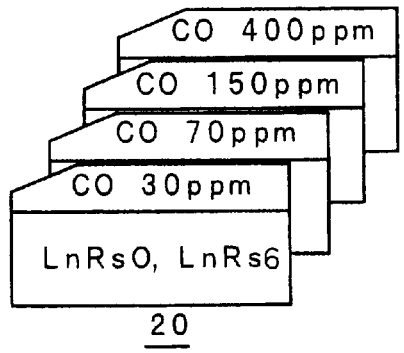
FIG. 35 is a diagram showing the data contents in an EEPROM of the most preferred embodiment.
FIG. 36 is a diagram showing the RAM data of a microprocessor of the most preferred embodiment.

The configuration of the stored data (calibration data) in the EEPROM 20 is shown in FIG. 35. The data configuration in the RAM 30 of the microcomputer 8 is shown in FIG. 36. The meanings of the variables are shown in Table 1.

Table 1

$LnRs0=X$: Sensor signal at the 0th second.
$LnRs6=Y$: Sensor signal at the 6th second.
A30–A400: Sensor signals at the 0th second in calibration in CO 30 ppm, 70 ppm, 150 ppm and 400 ppm.
B30–B400: Sensor signals at the 6th second in calibration in CO 30 ppm, 70 ppm, 150 ppm and 400 ppm.
[COA]: CO concentration before temperature compensation and humidity compensation.
[COB]: CO concentration after humidity compensation.
F: Internal ratio or external ratio of Ai and (Ai+1). Ai and (Ai+1) are two values closest to X selected from A30–A400.
J: Flag value.
B: Standard signal for comparison with the 6th second signal.
$B=(1-F)\cdot(Bi+F)\cdot(Bi+1)$. i and (i+1) are defined in a manner similar to Ai and (Ai+1).
K: Comparison constant. $K=Y-B$.
*1: Standard data are stored in the EEPROM.
*2: The look-up table may be expanded to add temperature compensation with the thermistor signal.

Figure 37:
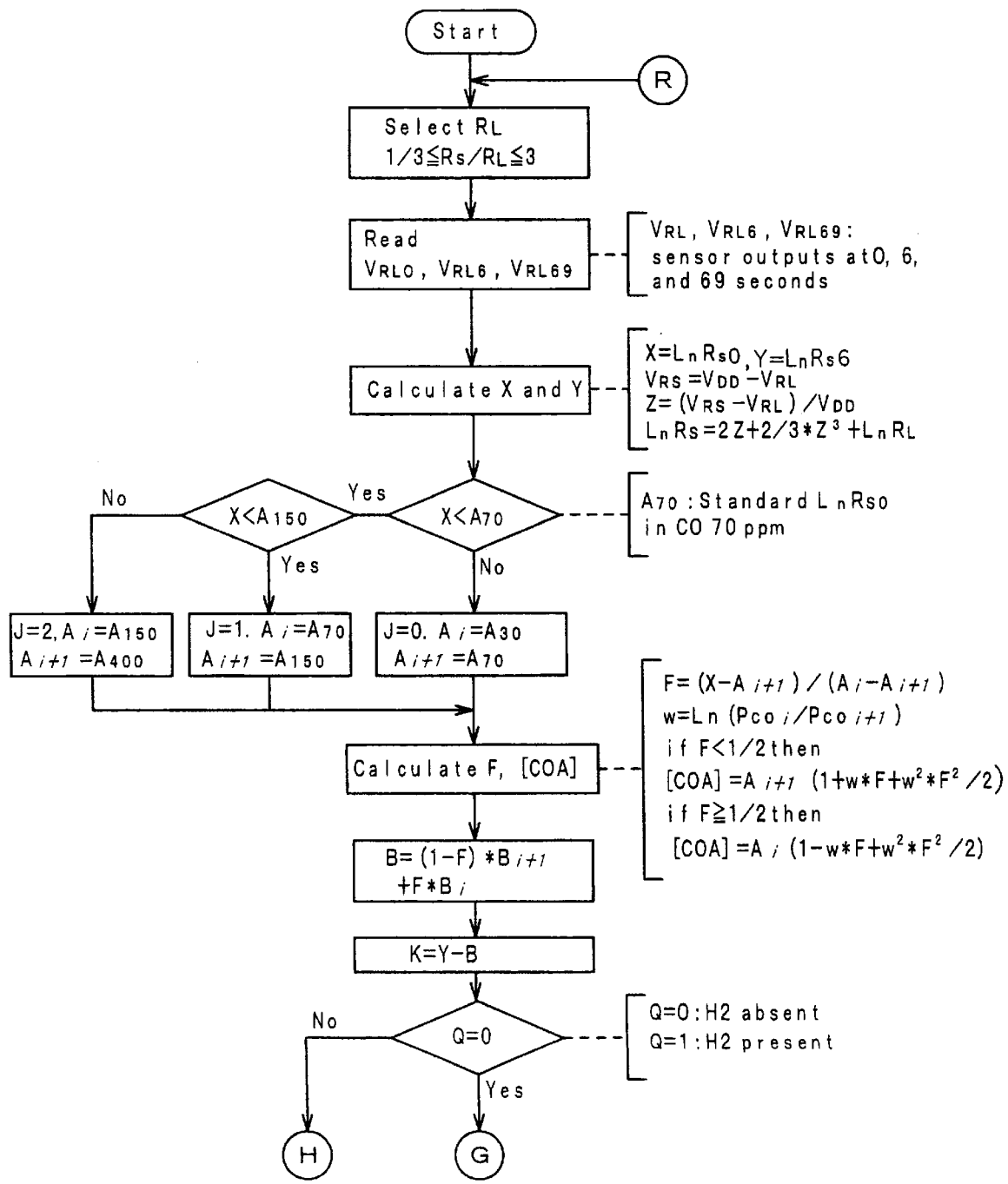
FIG. 37 is a flow chart of the operation of the most preferred embodiment, showing calculation of a distance K from a gas concentration axis.
Figure 38:
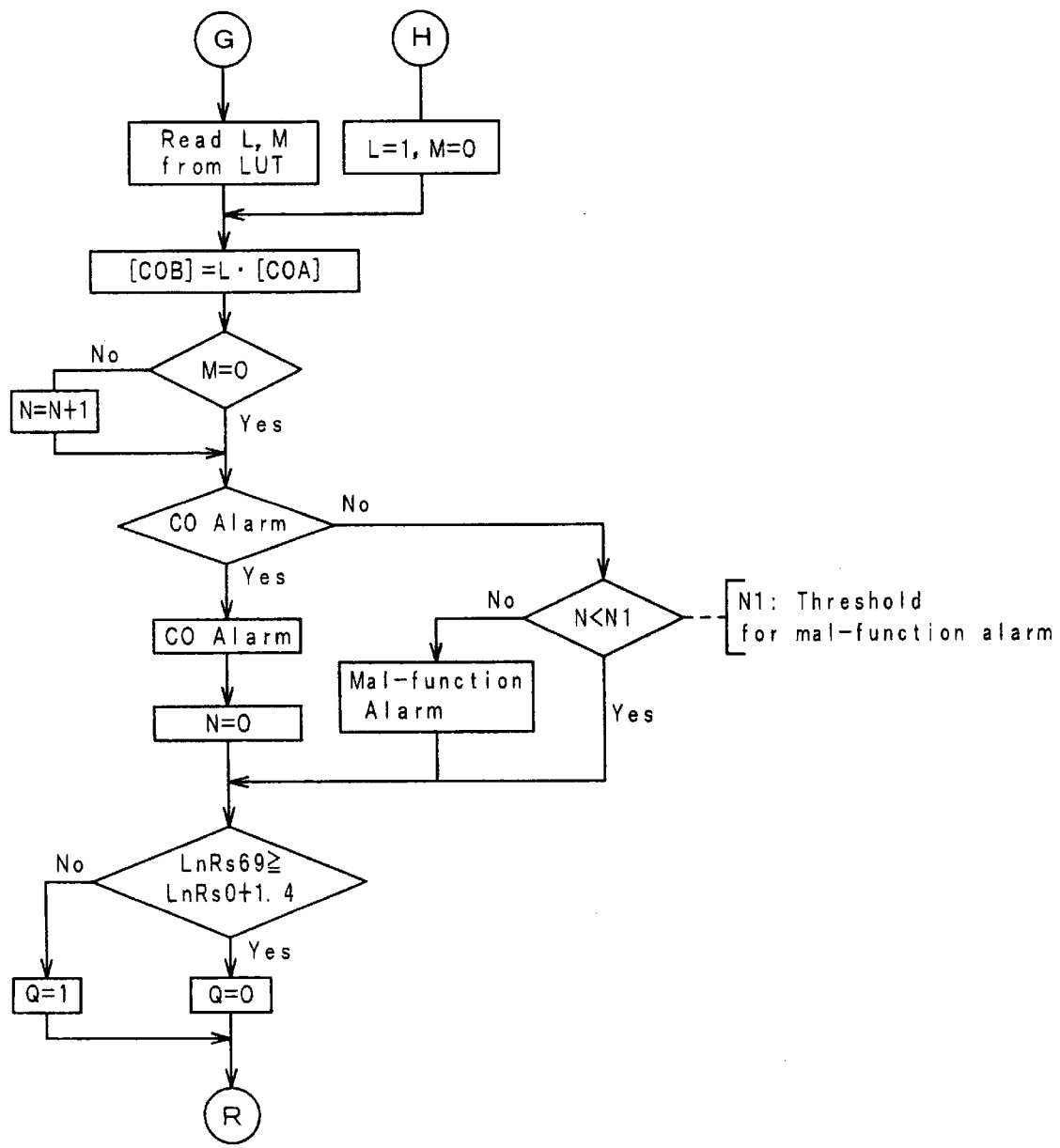
FIG. 38 is a flow chart of the operation of the most preferred embodiment, showing calculation of a compensation constant L and detection of mal-function alarm and hydrogen.

Processing of sensor signals is shown in FIG. 37 and FIG. 38. While the value of the ladder resistance 5 is switched so that, for example, Rs/RL is equal to or greater than ⅓ and equal to or less than 3, the sensor output at the 0th second V RL0, the sensor output at the 6th second V RL6, and the sensor output at the 69th second V RL69 are sampled. They are used to determine the values of X and Y. Then the CO concentration without compensation is checked whether it is equal to or less than 70 ppm (J=0), greater than 70 ppm and less than 150 ppm (J=1), or equal to or greater than 150 ppm (J=2). The internal ratio F and the CO concentration without compensation [COA] are determined. Next, the internal ratio thus determined is used to determine the value B corresponding to LnR6 when (X, Y) is assumed to be on the gas concentration line. Then, the difference between the actual resistance at the 6th second Y and B is defined as K, and compensation is given according to the magnitude of K. The process differs depending on presence or absence of hydrogen; when hydrogen is not present, the value of K is used to find the compensation constant L from the look-up table. The values of M for malfunction are also written in the look-up table. When the absolute value of K is extremely large, M will take a significant value (value other than 0). When hydrogen is detected, detection of malfunction will not be made, compensation is terminated, and the value of L is forced to be 1. Next, the CO value without compensation [COA] is multiplied with L to determine the CO concentration after compensation [COB]. Furthermore, if the value of M is not 0, 1 is added to the variable N that is related to malfunction. Now, the CO value after compensation [COB] exceeds the detection threshold, a CO alarm will be given and N will be reset to zero. On the other hand, when the CO alarm conditions are not met, if N is equal to or greater than the threshold N1 of malfunction, an alarm of malfunction will be given (LEDs 39, 40 will be flickered alternately). When the logarithm of the sensor resistance at the 69th second is not greater than the logarithm of the sensor resistance at the 0th second by 1.4 or over, the value of Q will be set to be 1; this means hydrogen is present. These steps are repeated with a period of 150 seconds.

Figure 39:
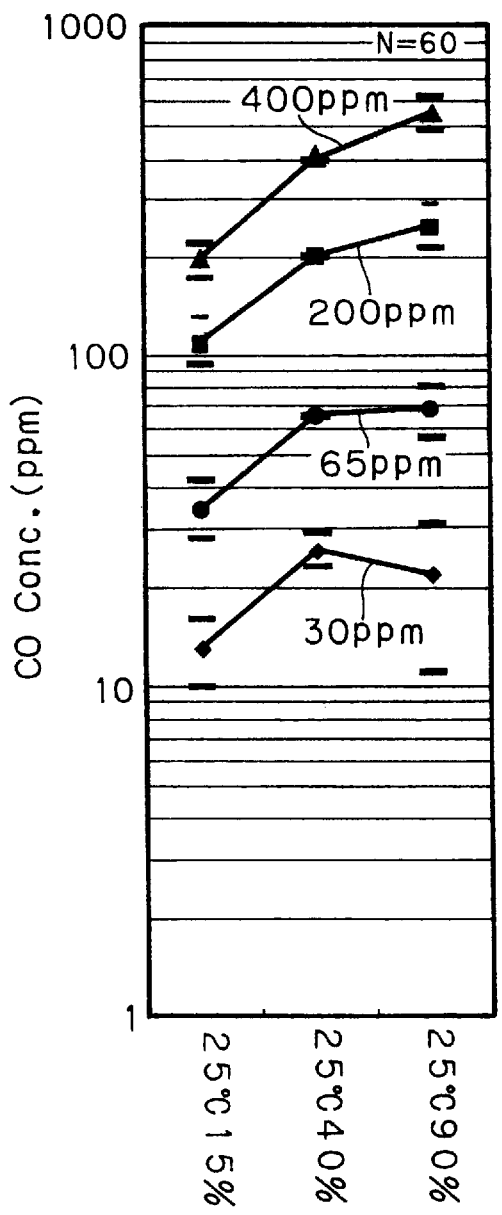
FIG. 39 shows a relative humidity dependence of the gas sensor used in the embodiment. The axis of ordinate indicates the output gas concentration, and the number of samples is 60.
Figure 40:
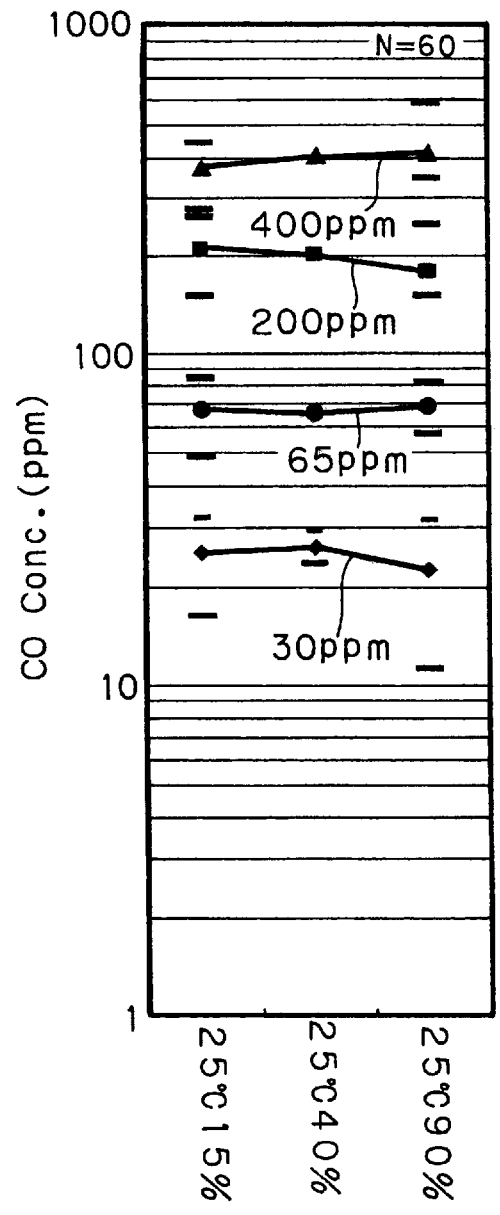
FIG. 40 is a characteristic diagram showing the relative humidity dependence in the most preferred embodiment. The axis of ordinate indicates the output gas concentration, and the number of samples is 60.

The results of processing of FIG. 37 and FIG. 38 are shown in FIG. 40. FIG. 39 is raw data for this purpose and indicates the value of [COA]. FIG. 40 shows the CO concentration after compensation [COB] that corresponds to the data of FIG. 39. The number of sensors is 60. The upper and lower marks on the data of each concentration are the maximum and the minimum of the output distribution. In the most preferred embodiment, the relative humidity dependence is substantially.

Figure 41:
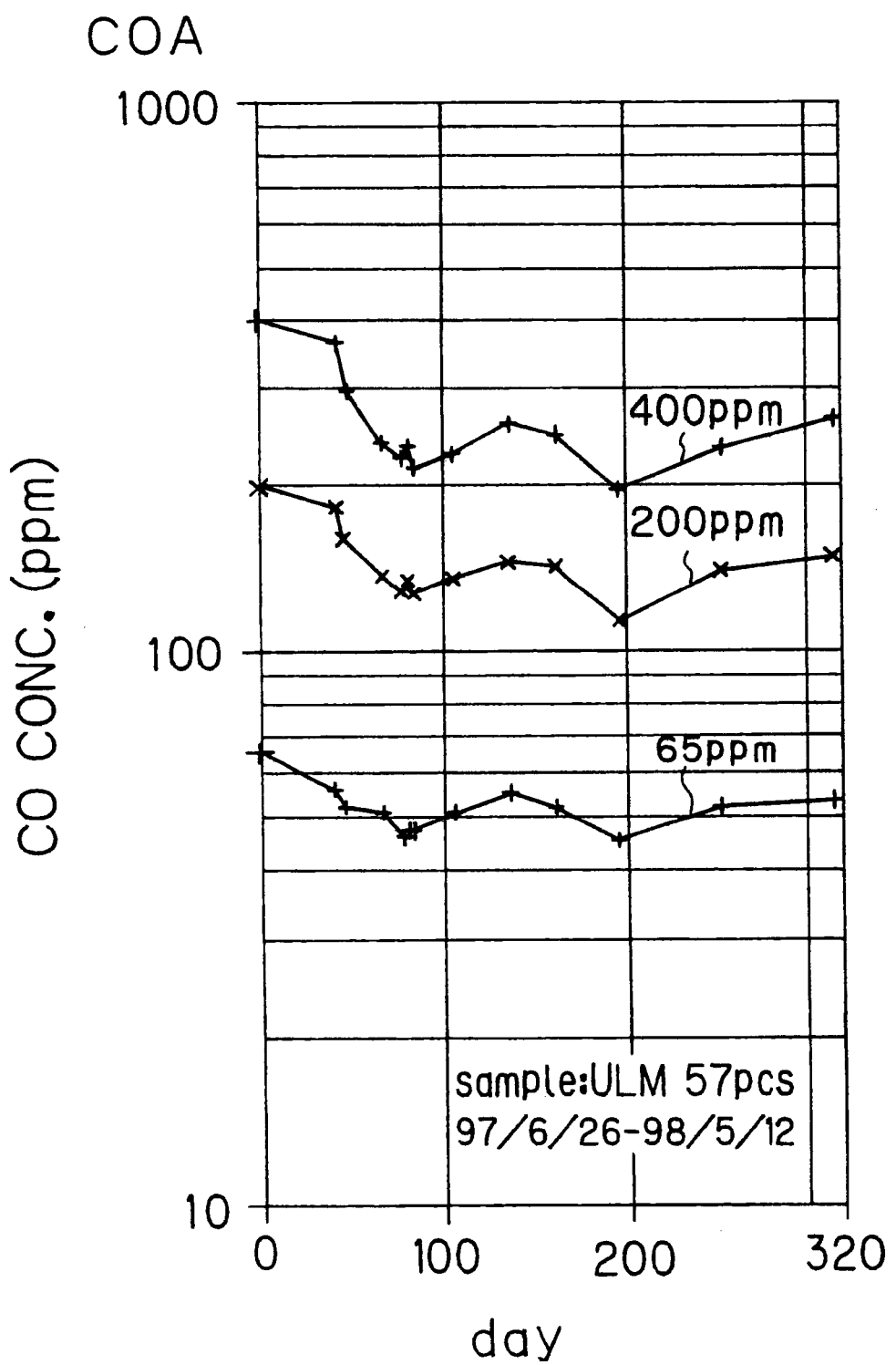
FIG. 41 is a characteristic diagram, for about one year, of the gas sensor used in the embodiment. The axis of ordinate indicates the output gas concentration. The gas sensor was left to stand for first one month, then its service was started. The number of samples is 57.
Figure 42:
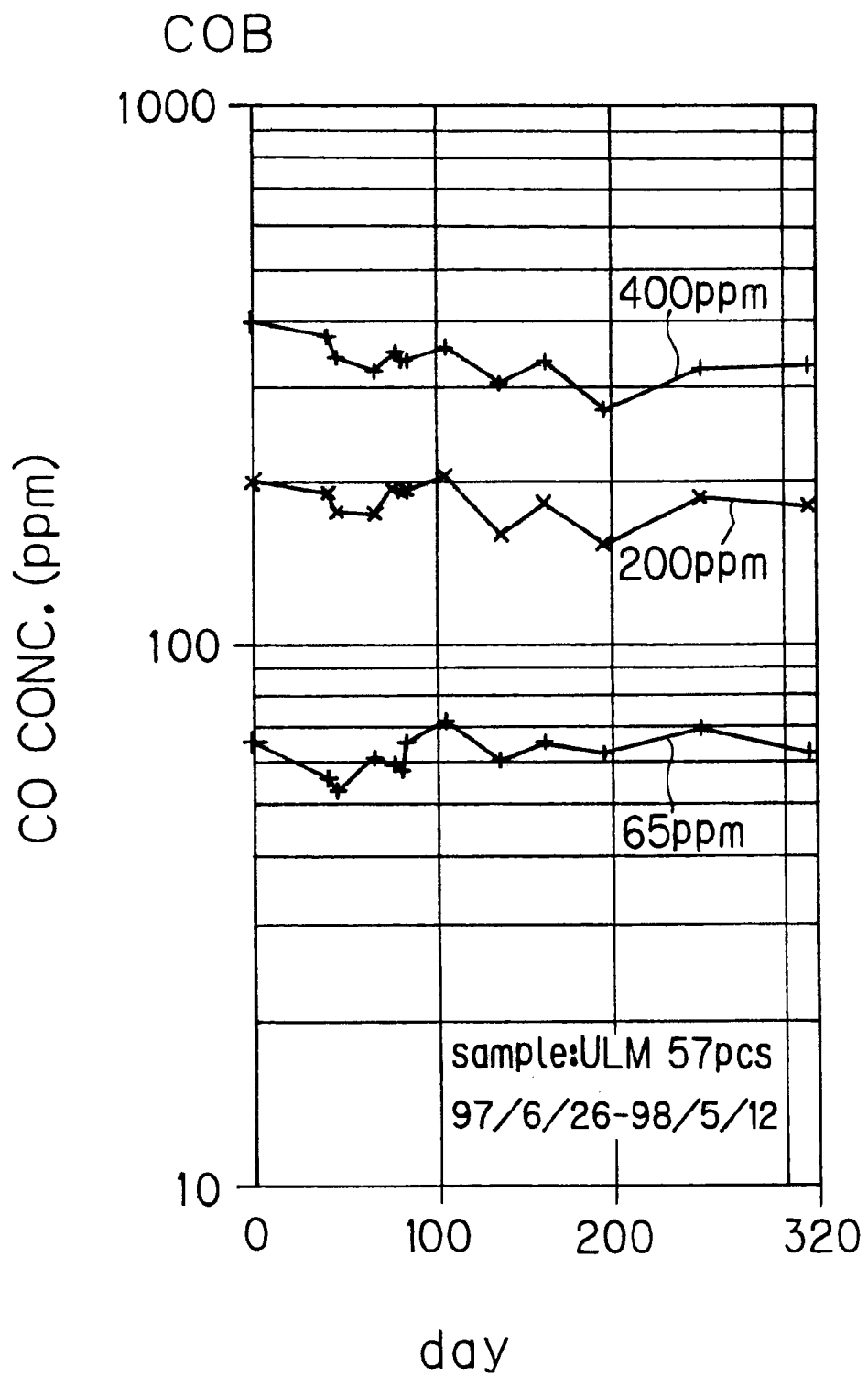
FIG. 42 is a characteristic diagram, for about one year, in the most preferred embodiment, showing the results of compensation of the data of FIG. 41 by the most preferred embodiment.

The characteristics of 57 samples of the sensor for about one year when the process of FIG. 37 and FIG. 38 were made are indicated. FIG. 41 indicates data that are equivalent to [COA]. FIG. 42 indicates the behaviors of the signals after compensation [COB]. The output of the sensor was measured in three concentrations CO 65 ppm, 200 ppm and 400 ppm; the sensors were left to stand in the first 30 days. After that, the sensors were used indoors in Japan, in natural atmosphere for about 300 days. In FIG. 37 and FIG. 38, as [COB] is compensated with intervals of 40%, and the compensation constant L is selected according to the humidity dependence, drift is designed to be compensated for about one half thereof. FIG. 42 shows the amplitude of the drift was successfully reduced to about one half for one year.

What is claimed is:

1. A method of detecting a gas by subjecting a metal oxide semiconductor gas sensor to a temperature change pattern, a resistance of said gas sensor changing with the temperature, said method of detecting a gas comprising:
   (a) defining a phase space, first and second coordinates of said phase space respectively representing magnitudes of first and second gas sensor signals, said first and second gas sensor signals respectively being responsive to the resistance of said gas sensor at first and second times after a start of the temperature change pattern;
   (b) for each concentration of plural concentrations of the gas to be detected, measuring at least said first and second gas sensor signals to thereby determine a first data point in said phase space;
   (c) storing data representing a locus in said phase space as a function of each first data point determined in step (b);
   (d) measuring at least said first and second gas sensor signals for determining a measurement point in said phase space at a time of measurement; and
   (e) determining a gas concentration from one of a projection along an axis from said measurement point to said locus and a distance between said locus and said measurement point.

2. A method of detecting a gas by subjecting a metal oxide semiconductor gas sensor to a temperature change pattern, a resistance of said gas sensor changing with the temperature, said method of detecting a gas comprising:
   (a) defining a phase space, first and second coordinates of said phase space respectively representing magnitudes of first and second gas sensor signals, said first and second gas sensor signals respectively being responsive to the resistance of said gas sensor at first and second times after a start of the temperature change pattern;
   (b) for each concentration of plural concentrations of the gas to be detected, measuring at least said first and second gas sensor signals to thereby determine a first data point in said phase space;
   (c) storing data representing a locus in said phase space as a function of each first data point determined in step (b);
   (d) measuring at least said first and second gas sensor signals for determining a measurement point in said phase space at a time of measurement; and
   (e) determining a gas concentration as a function of said measurement point and said locus.

3. A method of detecting a gas of claim 2 further comprising:
   (f) at a single concentration of the gas to be detected, measuring at least said first and second gas sensor signals a plurality of times to thereby determine a plurality of second data points in said phase space; and
   (g) storing data representing a deviation axis in said phase space as a function of said second data points determined in stop (f); and
   wherein step (e) includes storing data representing, in said phase space, a gas concentration axis as a function of each first data point determined in step (b); and
   wherein step (e) includes determining a gas concentration from a projection along an axis, which is parallel to said deviation axis, from said measurement point to said gas concentration axis.

4. A method of detecting a gas of claim 3 further comprising:
   limiting the projection according to a distance from the gas concentration axis.

5. A method of detecting a gas of claim 2 further comprising:
   defining a second phase space for detecting a coexisting gas; and
   measuring the coordinates of gas sensor signals in this second phase space.

6. A detector for detecting a gas by subjecting a metal oxide semiconductor gas sensor to a temperature change pattern, a resistance of said gas sensor changing with the gas, said detector for detecting a gas comprising:
   means for determining a phase space, first and second coordinates of said phase space respectively representing magnitudes of first and second gas sensor signals, said first and second gas sensor signals respectively being responsive to the resistance of said gas sensor at first and second times after a start of the temperature change pattern;
   storage means for storing a locus of first points in said phase space, each first point representing a measurement of said first and second gas sensor signals in a corresponding concentration of the gas to be detected, at least two corresponding concentrations being different from each other;

means for measuring at least said first and second gas sensor signals for determining a measurement point in said phase space; and means for determining a gas concentration as a function of said measurement point and said locus.

7. A detector for detecting a gas of claim 6 wherein said storage means stores, in said phase space, two intersecting axes including a gas concentration axis determined as a function of said first points and a deviation axis determined as a function of a plurality of second data points, each second data point representing a measurement of said first and second gas sensor signals in a single concentration of the gas to be detected, and said means for determining the gas concentration determines the gas concentration from a projection along an axis parallel to the deviation axis from said measurement point to said gas concentration axis.

8. An apparatus for detecting CO comprising:

a metal oxide semiconductor gas sensor having a heater and a resistance changing with CO;

means for applying electric power with a rectangular waveform to the heater so as to alternately change the temperature of the gas sensor between a higher temperature range and a lower temperature range;

means for sampling a gas sensor signal in the lower temperature range;

means for sampling a gas sensor signal during a shift from the lower temperature range to the higher temperature range, after an occurrence of a minimum of the resistance of the metal oxide semiconductor, and before the temperature of the gas sensor reaches a constant temperature in the higher temperature range; and CO detecting means for detecting CO in response to the gas sensor signal sampled during the shift from the lower temperature range to the higher temperature range.

9. A method of detecting a gas by subjecting of at least one gas sensor to a temperature change pattern, said at least one gas sensor outputting first and second gas sensor signals, said first and second gas sensor signals respectively being responsive to the resistance of the gas sensor signals at first and second times after the start of the temperature change pattern, the method comprising:

(a) measuring the first and second gas sensor signals of the at least one gas sensor in a first gas concentration;

(b) determining a first point in a phase space based upon the first and second gas sensor signals measured in step (a);

(c) aging the gas sensor;

(d) re-measuring the first and second gas sensor signals of the at least one gas sensor in the first gas concentration;

(e) determining a second point in the phase space based upon the first and second gas sensor signals measured in step (d);

(f) determining a drift direction based upon the first point and the second point in the phase space;

(g) measuring the first and second gas sensor signals of the at least one gas sensor in a second gas concentration;

(h) determining a third point in the phase space based upon the first and second gas sensor signals measured in step (g); and (i) determining the concentration of the second gas concentration as a function of the third point determined in step (h) and the drift direction determined in step (f).

10. A method of detecting a gas by subjecting at least one gas sensor to a temperature change pattern, said at least one gas sensor outputting first and second gas sensor signals, said first and second gas sensor signals respectively being responsive to the resistance of the gas sensor at first and second times after the start of the temperature change pattern, the method comprising:

(a) measuring the first and second gas sensor signals of the at least one gas sensor in a first gas concentration;

(b) determining a first point in a phase space based upon the first and second gas sensor signals measured in step (a);

(c) changing the humidity in the first gas concentration;

(d) re-measuring the first and second gas sensor signals of the at least one gas sensor in the first gas concentration;

(e) determining a second point in the phase space based upon the first and second gas sensor signals measured in step (d);

(f) determining a drift direction based upon the first point and the second point in the phase space;

(g) measuring the first and second gas sensor signals of the at least one gas sensor in a second gas concentration;

(h) determining a third point in the phase space based upon the first and second gas sensor signals measured in step (g); and (i) determining the concentration of the second gas concentration as a function of the third point measured in step (h) and the drift direction determined in step (f).

* * * * *